US 6,870,042 B1

(12) United States Patent
Schlievert et al.

(10) Patent No.: US 6,870,042 B1
(45) Date of Patent: Mar. 22, 2005

(54) MUTANTS OF STREPTOCOCCAL TOXIN A AND METHODS OF USE

(75) Inventors: Patrick M. Schlievert, Edina, MN (US); Manuela Roggiani, Minneapolis, MN (US); Jennifer Stoehr, Vadnais Heights, MN (US); Douglas Ohlendorf, Eden Prairie, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 10/625,221

(22) Filed: Jul. 22, 2003

Related U.S. Application Data

(60) Division of application No. 08/973,391, filed on Mar. 12, 1998, now Pat. No. 6,632,441, which is a continuation-in-part of application No. 08/480,261, filed on Jun. 7, 1995, now abandoned.

(51) Int. Cl.[7] .............................................. C07H 21/04
(52) U.S. Cl. .................. 536/23.7; 435/320.1; 536/24.1
(58) Field of Search .............................. 536/23.7, 24.1; 435/320.1, 69.1

(56) References Cited

U.S. PATENT DOCUMENTS

| 5,298,396 A | 3/1994 | Kotzin et al. |
| 5,336,598 A | 8/1994 | Kotzin et al. |

FOREIGN PATENT DOCUMENTS

| WO | WOA85 00832 | 2/1985 |
| WO | WO 93/14634 | 8/1993 |

OTHER PUBLICATIONS

Acharya, K. et al., "Structural Basis of Superantigen Action Inferred from Crystal Structure of Toxic–Shock Syndrome Toxin–1", Nature 367:94–97 (1994).
Aiyar, A. et al., "Modification of the Megaprimer Method of PCR Mutagenesis: Improved Amplification of the Final Product", BioTechniques vol. 14, No. 3 (1993) pp. 366–369.
Altschyl, S. et al., "Optimal Sequence Alignment Using Affine Gap Costs", Bulletin of Math. Biol. 48:603–616 (1986).
Anthony–Cahil, S. et al., "Site–specific mutagenesis with unnatural amino acids", Trends in Biochem. Sci. 14:400–403 (1989).
Barsumian et al., "Nonspecific and Specific Immunological Mitogenicity by Group A Streptococcal Pyrogenic Exotoxins", Infection and Immunity 22:681–688 (1978).
Belani, K. et al., Association of exotoxin–producing Group A streptococci and severe disease in children, Pediatr. Infect. Dis. J. 10:351–354 (1991).
Betley et al., "Staphylcoccal Enterotoxins, Toxic Shock Syndrome Toxin and Streptococcal Pyrogenic Exotoxins: A Comparative Study of their Molecuar Biology", Chem. Immun. 55:1–35 (1992).

Birkhaug et al., "Studies in Scarlet Fever II: Studies on the Use of Convalescent Scarlet Fever Serum in Dochez Scarletino Antistreptococcie serum for the treatment of scarlet fever", Bull. John Hopkins Hosp. 36:134–171 (1925).
Black, C.M. et al., "Detection of Streptococcal Pyrogenic Exotoxin Genes by a Nested Polymerase Chain Reaction", Molecular and Cellular Probes, vol. 7, pp. 255–259 (1993).
Bohach et al., "Staphylcoccal and Streptococcal Pyrogenic Toxins Involved in Toxic Shock Syndrome and Related Illnesses", Crit. Rev. Microbiol. 17:251–272 (1989).
Bowie, J. et al., "Deciphering the Message in Protein Sequences: Tolerance to Amino Acid Substitutions", Science 247:1306–1310 (Mar. 16, 1990).
Braunstein, N. et al., "Sequences in Both Class II Major Histocompatibility Complex a and β Chains Contribute to the Binding of the Superantigen Toxic Shock Syndrome Toxin 1", J. Exper. Med. 175:1301–1305 (Apr. 1, 1992).
Dohlsten et al., "Superantigen Induced Cytokines Supress Growth of Human Colon Carcinoma Cells", Int. J. Cancer 54:482–488 (1993).
Fast, D. et al., "Toxic Shock Syndrome–Associated Staphylcoccal and Streptococcal Pyrogenic Toxins are Potent Inducers of Tumor Necrosis Factor Production", Infection and Immunity 57:291–295 (Jan. 1989).
Goshorn, S. et al., "Cloning and characterization of the gene, speC, for pyrogenic exotoxin type C from Streptococcus pyogenes", Mol. Gen. Genet. 212:66–70 (1988).
Goshorn, S. et al., "Nucelotide Sequence of Streptococcal Pyrogenic Exotoxin Type C", Infection and Immunity 56:2518–2520 (1988).
Griggs, N. et al., "Mapping of Multiple Binding Domains of the Superantigen Staphylococcal Enterotoxin A for HLA", J. Immunology 148:2516–2521 (Apr. 15, 1992).
Hartwig, U. et al., "Mutations affecting MHC class II binding of the superantigen streptococcal erythrogenic toxin A." International Immunology 5(8):869–875.
Hattori, M. et al., "Structure of the rat $\alpha_2$—macroglobulin–coding gene", Gene 77:333–340 (1989).
Hauser, A. et al., "Molecular Analysis of Pyrogenic Exotoxins from Streptococcus pyogenes Isolates Associated with Toxic Shock–Like Syndrome", J. Clin. Microbiol. 29:1562–1567 (Aug. 1991).
Hedlund et al., "Superantigen–Based Tumor Therapy in Vivo Activation of Cytotoxic T Cells", Cancer Immun. Immunother. 36:89–93 (1993).

(List continued on next page.)

Primary Examiner—Jennifer E. Graser
(74) Attorney, Agent, or Firm—Merchant & Gould P.C.

(57) ABSTRACT

This invention is directed to mutant SPE-A toxins or fragments thereof, vaccine and pharmaceutical compositions, and methods of using the vaccine and pharmaceutical compositions. The preferred SPE-A toxin has at least one amino acid change and is substantially non-lethal compared with the wild type SPE-A toxin. The mutant SPE-A toxins can form vaccine compositions useful to protect animals against the biological activities of wild type SPE-A toxin.

19 Claims, 9 Drawing Sheets

OTHER PUBLICATIONS

Hsiao, Ku–chuan et al., "A Fast and simple procedure for sequencing double stranded DNA with Seqenase", Nucleic Acids Research 19:2787 (1991).

Ihle et al., "Antibody Targeted Super Antigens Induce Lysis of Major Histocompatibility Complex Class II Negative T Cell Leukemia Lines", Cancer Res. 55:623–628 (1995).

Iwasaki et al., "Cloning, Characterization and Overexpression of Streptococcus Pyogenes Gene Encoding a New Type of Mitogenic Factor", FEBS Lett. 331:187–192 (1993).

Jardetzky, T. et al., "Three–dimensional structure of a human class II histocompatibility molecule complexed with super-antigen", Nature 368:711–718 (Apr. 21, 1994).

Jett et al., "Identification of Staphylcoccal Enerotoxin B Sequences Important for Induction of Lymphocyte Proliferation Using Synthetic Peptide Fragments of the Toxin", Infection and Immunity 62:3408–3415 (1994).

Johnson, L. et al., "Group A streptococcal phage T12 carries the structural gene for pyrogenic exotoxin type A", Mol. Gen. Genet. 194:52–56 (1994).

Kappler, J. et al., "Mutations Defining Functional Regions of the Superantigen Staphylcoccal Enterotoxin B.", J. Exp. Med. 175:387–396 (Feb. 1992).

Lee, P. et al., "Effects of Staphylococcal Toxic Shock Syndrome Toxin I on Aortic Endothelial Cells", J. Infect. Dis. 164:711–9 (1991).

Lee, P. et al., "Fluid Replacement Protection of Rabbits Challenged Subcutanteously with Toxic Shock Syndrome Toxins", Infection and Immunity 59(3):879–884 (Mar. 1991).

Marrack, P. et al., "The Staphylcoccal Enterotoxins and Their Relatives", Science 248:705–711 (May 1990).

Martin, D., et al., Molecular Epidemiology of Group A Streptococcus M Type 1 Infections, J. Infect. Dis. 167:1112–7 (1993).

Mollick, J. et al., "Localization of a Site on Bacterial Superantigens That Determines T Cell Receptor β Chain Specificity", J. Exp. Med. 177:283–293 (Feb. 1993).

Mollick, J. et al., "Novel Superantigen Isolated from Pathogenic Strains of Streptococcus pyogenes with Aminoterminal Homology to Staphylcoccal Enterotoxins B and C", J. Clin. Invest. 92:710–719 (Aug. 1993).

Murray, D. et al., "Immunobiologic and Biochemical Properties of Mutants of Toxic Shock Syndrome Toxin–1", J. Immunol (US) (1994) 152(1):87–95.

Musser et al., "Streptococcus Pyogenes Causing Toxic Shock–like Syndrome and Other Invasive Diseases: Colonal Diversity and Pyrogenic Exotoxin Expression", Proc. Nat'l. Acad Sci. (USA) 88:2668–2672 (1991).

Musser, J. et al., "Infect Immun", Mar. 1995, 63(3) P994–1003.

Nelson, K. et al., "Characterization and Clonal Distribution of Four Alleles of the speA Gene Encoding pyrogenic Exotoxin A (Scarlet Fever Toxin) in *Streptococcus pyogenes*", . Exp. Med., 174:1271–1274 (Nov. 1991).

Norrby–Teglund, A. et al., "Relation between Low Capacity of Human Sera to Inhibit Streptococcal Mitogens and Serious Manifestation of Disease", J. Infect. Dis. 170:585–91 (1994).

Perrin, S. et al., "Site–specific mutagenesis using asymmetric polymerase chain reaction and a single mutant primer", Nucleic Acids Research 18:7433–7438 (1990).

Prasad, G. et al., "Structure of Toxic Shock Syndrome Toxine 1", Biochemistry vol. 32, No. 50 (Dec. 21, 1993) 50:13761–13766.

Rennell, D. et al., "Systematic Mutation of Bacteriophage T4 Lysozyme", J. Mol. Biol. 222:67–87 (1991).

Revie, D., et al., "Kinetic analysis for optimization of DNA ligation reactions", Nucleic Acids Research 16:10301–10321 (1988).

Roggiani, A. et al., "Localization of biological activities of Streptococcal Pyrogenic Exotoxin", poster presentation at the ASM 94th General Meeting, Las Vegas, Nevada (1994).

Schlievert et al., "Group B Streptococcal Toxic Shock–Like Syndrome: Report of a Case and Purification of Associated Pyrogenic Toxin", Clin. Infect. Dis. 17:26–31 (1993).

Schlievert,"Role of Superantigens in Human Disease", J. Infect. Dis. 167:997–1002 (1993).

Schlievert, P. et al., "Infect Immun", Jun. 1989, 57 (6) P1865–7.

Scott et al., Characterization of Staphylcoccus aureus Isolates from Patients with Toxic Shock Syndrome, Using Polyethylene Infection Chambers in Rabbits, Infection and Immunity 39:383–387 (Jan. 1983).

Swaminathan, "Crystal Structure of Staphococcal Enterotoxin B as Superantigen", Nature 359:801–806 (1992).

Tomai, M. et al., "Distinct T–Cell Receptor Vβ Gene Usage by Human T. Lymphocytes Stimulated with the Streptococcal Pyrogenic Exotoxins and pep M5 Protein", Infection and Immunity 60:701–705 (Feb. 1992).

Wallace, C., Understanding cytochrome c function: engineering protein structure by semisynthesis, FASEB Journal 7:505–515 (1993).

Weeks et al., "Nucleotide Sequence of the Type A Streptococcal Exotoxin (Erythrogenic Toxin) Gene from Streptococcus pyogenes Bacteriophage T12", Infection and Immunology, Apr. 1986, 52:144–150, pp. 144–150.

DOMAIN B          DOMAIN A

```
TCATGTTTGACAGCTTATCATCGATAAGCTTACTTTTCGAATCAGGTCTATCCTTGAAACAGGTGCAACATAGATTAGGGCATGGAGATTTACCAGACAA
                     50                                                                          100

CTATGAACGTATATACTCACATCACGCAATCGGCAATTGATGACATTGGAACTAAATTCAATCAATTTGTTACTAACAAGCAACTAGATTGACAACTAAT
                     150                                                                         200

TCTCAACAAACGTTAATTTAACAACATTCAAGTAACTCCCACCAGCTCCATCAATGCTTACCGTAAGTAATCATAACTTACTAAAACCTTGTTACATCAA
                     250                                                                         300

GGTTTTTCTTTTTGTCTTGTTCATGAGTTACCATAACTTTCTATATTATTGACAACTAAATTGACAACTCTTCAATTATTTTTCTGTCTACTCAAAGTT
                     350                                                                         400

TTCTTCATTTGATATAGTCTAATTCCACCATCACTTCTTCCACTCTCTCTACCGTCACAACTTCATCATCTCTCACTTTTTCGTGTGGTAACACATAATC
                     450                                                                         500

AAATATCTTTCCGTTTTTACGCACTATCGCTACTGTGTCACCTAAAATATACCCCTTATCAATCGCTTCTTTAAACTCATCTATATATAACATATTTCAT
                     550                                                                         600

CCTCCTACCTATCTATTCGTAAAAAGATAAAAATAACTATTGTTTTTTTTGTTATTTTATAATAAAATTATTAATATAAGTTAATGTTTTTAAAAATAT
                     650                                                                         700

ACAATTTTATTCTATTTATAGTTAGCTATTTTTTCATTGTTAGTAATATTGGTGAATTGTAATAACCTTTTTAAATCTAGAGGAGAACCCAGATATAAAA
                     750                                                                         800

M  E  N  N  K  K  V  L  K  K  M  V  F  F  V  L  V  T  F  L  G  L
TGGAGGAATATTA      ATG GAA AAC AAT AAA AAA GTA TTG AAG AAA ATG GTA TTT TTT GTT TTA GTG ACA TTT CTT GGA CTA

10
T  I  S  Q  E  V  F  A  Q  Q  D  P  D  P  S  Q  L  H  R  S  S  L  V  K  N  L
ACA ATC TCG CAA GAG GTA TTT GCT CAA CAA GAC CCC GAT CCA AGC CAA CTT CAC AGA TCT AGT TTA GTT AAA AAC CTT 20                                     30                                  40
Q  N  I  Y  F  L  Y  E  G  D  P  V  T  H  E  N  V  K  S  V  D  Q  L  L  S  H
CAA AAT ATA TAT TTT CTT TAT GAG GGT GAC CCT GTT ACT CAC GAG AAT GTG AAA TCT GTT GAT CAA CTT TTA TCT CAC 50                                  60                                  70
D  L  I  Y  N  V  S  G  P  N  Y  D  K  L  K  T  E  L  K  N  Q  E  M  A  T  L
GAT TTA ATA TAT AAT GTT TCA GGG CCA AAT TAT GAT AAA TTA AAA ACT GAA CTT AAG AAC CAA GAG ATG GCA ACT TTA 80                                  90
F  K  D  K  N  V  D  I  Y  G  V  E  Y  Y  H  L  C  Y  L  C  E  N  A  E  R  S
TTT AAG GAT AAA AAC GTT GAT ATT TAT GGT GTA GAA TAT TAC CAT CTC TGT TAT TTA TGT GAA AAT GCA GAA AGG AGT 100                                    110                                 120
A  C  I  Y  G  G  V  T  N  H  E  G  N  H  L  E  I  P  K  K  I  V  V  K  V  S
GCA TGT ATC TAC GGA GGG GTA ACA AAT CAT GAA GGG AAT CAT TTA GAA ATT CCT AAA AAG ATA GTC GTT AAA GTA TCA 130                                 140
I  D  G  I  Q  S  L  S  F  D  I  E  T  N  K  K  M  V  T  A  Q  E  L  D  Y  K
ATC GAT GGT ATC CAA AGC CTA TCA TTT GAT ATT GAA ACA AAT AAA AAA ATG GTA ACT GCT CAA GAA TTA GAC TAT AAA 150                                    160                                 170
V  R  K  Y  L  T  D  N  K  Q  L  Y  T  N  G  P  S  K  Y  E  T  G  Y  I  K  F
GTT AGA AAA TAT CTT ACA GAT AAT AAG CAA CTA TAT ACT AAT GGA CCT TCT AAA TAT GAA ACT GGA TAT ATA AAG TTC 180                                 190                                 200
I  P  K  N  K  E  S  F  W  F  D  F  P  P  E  P  E  F  T  Q  S  K  Y  L  M  I
ATA CCT AAG AAT AAA GAA AGT TTT TGG TTT GAT TTT TTC CCT GAA CCA GAA TTT ACT CAA TCT AAA TAT CTT ATG ATA 210                                 220
Y  K  D  N  E  T  L  D  S  N  T  S  Q  I  E  V  Y  L  T  T  K  *
TAT AAA GAT AAT GAA ACG CTT GAC TCA AAC ACA AGC CAA ATT GAA GTC TAC CTA ACA ACC AAG TAA CTTTTTCCTTTTCGC

AACCTTACCTACTGCTGCATTTAGAAATTTTATTGCAATTCTTTTATTAATGTAAAAACCGCTCATTTGATCACCGGTTTTGTCTTATCTAAAGCAGCTTTAC
                     1600                                                    1650

CTCCTAATGCTGCAAAATTTTAAATGTTGGATTTTTGTATTTGTCTATTGTATTTGATGGGTAATCCCATTTTTCGACAGACATCGTCGTGCCACCTCTAACA
                     1700                                                    1750

CCAAAATCATACACACGGACCTTGTAGCTTAGCAACTATTTTATCGTC    3'
  1800                             1837
```

FIG. 3

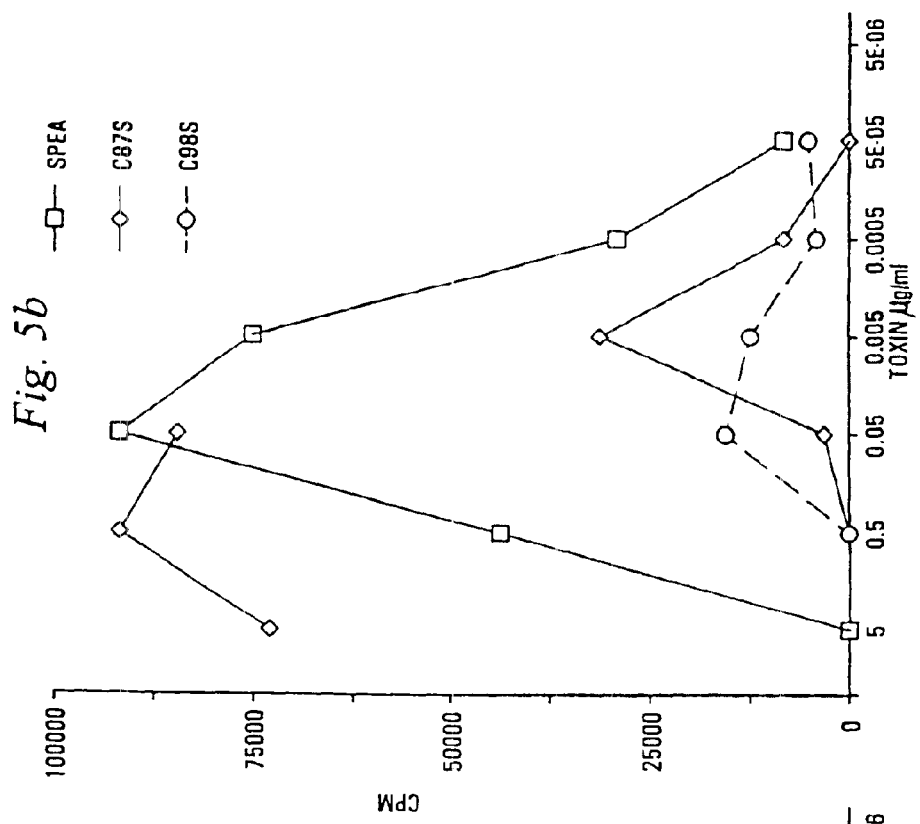
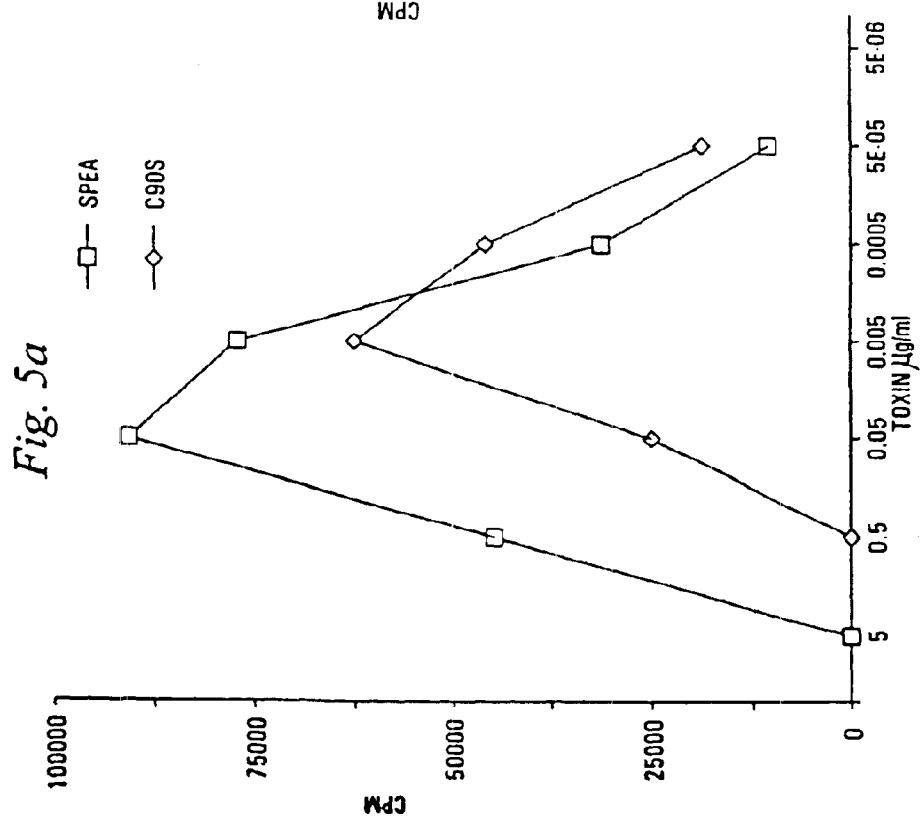

MUTANTS OF STREPTOCOCCAL TOXIN A AND METHODS OF USE

This application is a divisional of application Ser. No. 08/973,391, filed Mar. 12, 1998, now U.S. Pat. No. 6,632,441, issued Oct. 14, 2003, which is a continuation-in-part of application Ser. No. 08/480,261, filed Jun. 7, 1995, now abandoned, which applications are incorporated herein by reference.

BACKGROUND OF THE INVENTION

*Streptococcus pyogenes*, also known as β-hemolytic group A streptococci (GAS) is a pathogen of humans which can cause mild infections such as pharyngitis and impetigo. Post infection autoimmune complications can occur, namely rheumatic fever and acute glomerulonephritis. GAS also causes severe acute diseases such as scarlet fever and streptococcal toxic shock syndrome (STSS). Severe GAS infections were a large problem in the U.S. and throughout the world at the beginning of this century. In the mid-forties, the number of cases and their severity decreased steadily for yet not completely understood reasons. However, more recently, a resurgence of serious diseases caused by GAS has been seen such that there may be 10–20,000 cases of STSS each year in the United States. As many as 50 to 60% of these patients will have necrotizing fascitis and myositis; 30 to 60% will die and as many as one-half of the survivors will have limbs amputated.

In 1986 and 1987 two reports described an outbreak of severe GAS infections localized in the Rocky Mountain area. These reports have been followed in the past few years by several others describing a disease with analogous clinical presentation. The symptoms described for this disease were very similar to those described for toxic shock syndrome (TSS), and in 1992 a committee of scientists gave to this clinical presentation the formal name of STSS, and set the criteria for its diagnosis. STSS is defined by the presence of the following:

1. hypotension and shock;
2. isolation of group A streptococci;
3. two or more of the following symptoms: fever 38.5° C. or higher, scarlet fever rash, vomiting and diarrhea, liver and renal dysfunction, adult respiratory distress syndrome, diffuse intravascular coagulation, necrotizing fascitis and/or myositis, bacteremia.

Streptococcal isolates from STSS patients are predominantly of M type 1 and 3, with M18 and nontypable organisms making up most of the reminder. The majority of M1, 3, 18, and nontypable organisms associated with STSS make pyrogenic exotoxin A (SPE-A, scarlet fever toxin A). In contrast, only 15% of general streptococcal isolates produce this toxin. Moreover, administration of SPE-A to a rabbit animal model and in two accidental human inoculations can reproduce the symptoms of STSS.

SPE-A is a single peptide of molecular weight equal to 25,787 daltons, whose coding sequence is carried on the temperate bacteriophage T12. speA, the gene for SPE-A, has been successfully cloned and expressed in *Escherichia coli*. SPE-A is a member of a large family of exotoxins produced by streptococci and staphylococci, referred to as pyrogenic toxins based upon their ability to induce fever and enhance host susceptibility up to 100,000 fold to endotoxin.

Recently these toxins have been referred to as superantigens because of their ability to induce massive proliferation of T lymphocytes, regardless of their antigenic specificity, and in a fashion dependent on the composition of the variable part of the β chain of the T cell receptor. These toxins also stimulate massive release of IFN-γ, IL-1, TNT-α and TNF-β. Other members of this family are streptococcal pyrogenic exotoxins type B and C, staphylococcal toxic shock syndrome toxin 1, staphylococcal enteroxtoxins A, B, Cn, D, E, G and H, and non-group A streptococcal pyrogenic exotoxins. These toxins have similar biochemical properties, biological activities and various degrees of sequence similarity.

The most severe manifestations of STSS are hypotension and shock, that lead to death. It is generally believed that leakage of fluid from the intravascular to the interstitial space is the final cause of hypotension, supported by the observation that fluid replacement therapy is successful in preventing shock in the rabbit model of STSS described above. It has been hypothesized that SPE-A may act in several ways on the host to induce this pathology.

SPE-A has been shown to block liver clearance of endotoxin of endogenous flora's origin, by compromising the activity of liver Kuppfer cells. This appears to cause a significant increase in circulating endotoxin, that through binding to lipopolysaccharide binding protein (LBP) and CD14 signaling leads to macrophage activation with subsequent release of TNF-α and other cytokines. Support for the role of endotoxin in the disease is given by the finding that the lethal effects of SPE-A can be at least partially neutralized by the administration to animals of polymyxin B or by the use of pathogen free rabbits.

Another modality of induction of shock could be the direct activity of the toxin on capillary endothelial cells. This hypothesis stems from the finding that the staphylococcal pyrogenic toxin TSST-1 binds directly to human umbilical cord vein cells and is cytotoxic to isolated porcine aortic endothelial cells.

Another of the toxin's modality of action includes its superantigenicity, in which the toxin interacts with and activates up to 50% of the host T lymphocytes. This massive T cell stimulation results in an abnormally high level of circulating cytokines TNF-β and IFN-γ which have direct effects on macrophages to induce release of TNF-α and IL-1. These cytokines may also be induced directly from macrophages by SPE-A through MHC class II binding and signalling in the absence of T cells. The elevated levels of TNF-α and -β cause several effects typically found in Gram negative induced shock, among which is damage to endothelial cells and capillary leak. However, the administration to SPE-A treated rabbits of cyclosporin A, which blocks upregulation of IL-2 and T cell proliferation, did not protect the animals from shock, suggesting that additional mechanisms may be more important in causing capillary leak.

Thus, there is a need to localize sites on the SPE-A molecule responsible for different biological activities. There is a need to develop variants of SPE-A that have changes in biological activities such as toxicity and mitogenicity. There is a need to develop compositions useful in vaccines to prevent or ameliorate streptococcal toxic shock syndrome. There is also a need to develop therapeutic agents useful in the treatment of streptococcal toxic shock syndrome and other diseases.

SUMMARY OF THE INVENTION

This invention includes mutant SPE-A toxins and fragments thereof, vaccines and pharmaceutical compositions and methods of using vaccines and pharmaceutical compositions.

Mutant SPE-A toxins have at least one amino acid change and are substantially nonlethal as compared with a protein substantially corresponding to a wild type SPE-A toxin. For vaccine compositions, mutant toxins also stimulate a protective immune response to at least one biological activity of a wild type SPE-A toxin. Mutant toxins for vaccine compositions are optionally further selected to have a decrease in enhancement of endotoxin shock and a decrease in T cell mitogenicity when compared to the wild type SPE-A. An especially preferred mutant for vaccine compositions is one that has a change at an amino acid equivalent to amino acid 20 of a wild type SPE-A toxin. For pharmaceutical compositions, it is preferred that a mutant toxin is substantially nonlethal while maintaining T cell mitogenicity comparable to a wild type SPE-A toxin.

The invention also includes fragments of a wild type speA toxin and mutants of speA toxins. Fragments and peptides derived from wild type SPE-A are mutant SPE-A toxins. Fragments can include different domains or regions of the molecule joined together. A fragment is substantially nonlethal when compared to a wild type SPE-A toxin. For mutant toxins, a fragment has at least one amino acid change compared to a wild type SPE-A amino acid sequence. Fragments are also useful in vaccine and pharmaceutical compositions.

The invention also includes expression cassettes, vectors and transformed cells. An expression cassette comprises a DNA sequence encoding a mutant SPE-A toxin or fragment thereof operably linked to a promoter functional in a host cell. DNA cassettes are preferably inserted into a vector. Vectors include plasmids or viruses. Vectors are useful to provide template DNA to generate DNA encoding a mutant SPE-A toxin. DNA cassettes and vectors are also useful in vaccine compositions. Nucleic acids encoding a mutant SPE-A toxin or fragment thereof can be delivered directly for expression in mammalian cells. The promoter is preferably a promoter functional in a mammalian cell. Nucleic acids delivered directly to cells can provide for expression of the mutant SPE-A toxin in an individual so that a protective immune response can be generated to at least one biological activity of a wild type SPE-A toxin.

Additional vaccine composition include stably transformed cells or viral vectors including an expression cassette encoding a mutant SPE-A toxin or fragment thereof. Viral vectors such as vaccinia can be used to immunize humans to generate a protective immune response against at least one biological activity of a wild type SPE-A toxin. Transformed cells are preferably microorganisms such as *S. aureus*, *E. coli*, or *Salmonella* species spp. Transformed microorganisms either include mutant SPE-A toxin or fragment thereof on their surface or are capable of secreting the mutant toxin. Transformed microorganisms can be administered as live, attenuated or heat killed vaccines.

The invention also includes methods of using vaccines and pharmaceutical compositions. Vaccines are administered to an animal in an amount effective to generate a protective immune response to at least one biological activity of a wild type SPE-A toxin. Preferably, the vaccine compositions are administered to humans and protect against the development of STSS. Pharmaceutical compositions are used in methods of stimulating T cell proliferation. The pharmaceutical compositions are especially useful in the treatment of cancers that are treated with interleukins, interferons or other immunomodulators, T cell lymphomas, ovarian and uterine cancers. A pharmaceutical composition is administered to a patient having cancer.

The mutant SPE-A toxins and/or fragments thereof and other vaccine compositions can be useful to generate a passive immune serum. Mutant SPE-A toxins or fragments thereof, DNA expression cassettes or vectors, or transformed microorganisms can be used to immunize an animal to produce neutralizing antibodies to at least one biological activity of wild type SPE-A. The neutralizing antibodies immunoreact with a mutant SPE-A toxin and/or fragment thereof and the wild type SPE-A toxin. Passive immune serum can be administered to an animal with symptoms of A streptococcal infection and STSS.

BRIEF DESCRIPTION OF THE FIGURES

FIG. 3 shows the DNA sequence (SEQ ID NO:12) and predicted amino acid sequence (SEQ ID NO:13) of the cloned SPE-A toxin from T12.

FIGS. 5A and 5B T cell proliferation assay. Rabbit splenocytes were incubated in 96 well microtiter plates in quadruplicate with SPE-A, C87S-SPE-A, C98S-SPE-A, and C90S-SPE-A for 72 hours. Cells were pulsed with [$^3$H] thymidine for 18 to 24 hours, harvested onto filters, and [$^3$H] thymidine incorporation was measured in a scintillation counter. Results are expressed as counts per minute (CPM) versus concentrations of toxin in μg/ml. Data presented are from the most representative of three independent experiments.

FIG. 7. Superantigenicity of wild type SPEA compared to single mutant. Rabbit spleen cells were incubated for 4 days with SPEA or mutants at the indicated doses. Four replicate wells were used at each dose of SPEA and mutants. On day 3, 1 μCI $^3$H thymidine was added to each well. Superantigenicity index=$^3$H thymidine incorporation by splenocytes in the presence of SPEA or mutants divided by $^3$H thymidine incorporation in the absence of SPEA or mutants.

FIG. 8. Superantigenicity of wild type SPEA compared to double mutants. Methods used were those described in FIG. 7.

DETAILED DESCRIPTION OF THE INVENTION

This invention is directed to mutant SPE-A toxins and fragments thereof, vaccine and pharmaceutical compositions including mutant SPE A toxins or fragments thereof, methods of preparing mutant SPE-A toxins and fragments thereof, and methods of using SPE-A toxins and fragments thereof.

Mutant SPE-A toxins are proteins that have at least one amino acid change and have at least one change in a biological function compared with a protein substantially corresponding to a wild type SPE-A toxin. Preferably, the mutant SPE-A toxin is substantially nonlethal when compared to a wild type SPE-A toxin at the same dose. Mutant SPE-A toxins can be generated using a variety of methods including site-directed mutagenesis, random mutagenesis, conventional mutagenesis, in vitro mutagenesis, spontaneous mutagenesis and chemical synthesis. Mutant SPE-A toxins are preferably selected to: 1) ensure at least one change in an amino acid; and 2) to have a change in at least one biological function of the molecule preferably a decrease or elimination of systemic lethality. The mutant toxins are useful in vaccine compositions for protection against at least one biological activity of SPE-A toxin such as prevention or amelioration of STSS, in methods of treating animals with symptoms of STSS, and in methods for stimulating T cell proliferation and in the treatment of cancer. Single and double SPE-A mutants were tested and the antibody to the mutants inhibited cell responses to SPEA.

A. Mutant SPE-A Toxins or Fragments Thereof, Vaccine and Pharmaceutical Compositions The invention includes mutant SPE-A toxins that have at least one amino acid change and that have at least one change in a biological activity compared with proteins that substantially correspond to and have the same biological activities as wild type SPE-A.

Wild type SPE-A toxin is encoded by a gene speA found on bacteriophage T12. The wild type SPE-A toxin has a molecular weight of 25,787 Daltons as calculated from the deduced amino acid sequence of the mature protein. A DNA sequence encoding a wild type SPE-A toxin and the predicted amino acid sequence for a wild type SPE-A toxin is shown in FIG. 3. A DNA sequence encoding a wild type SPE-A toxin has been cloned in *E. coli* and *S. aureus*. Amino acid number designations in this application are made by reference to the sequence of FIG. 3 with glutamine at position 31 designated as the first amino acid. The first 30 amino acids represent a leader sequence not present in the mature protein.

Figure 1:
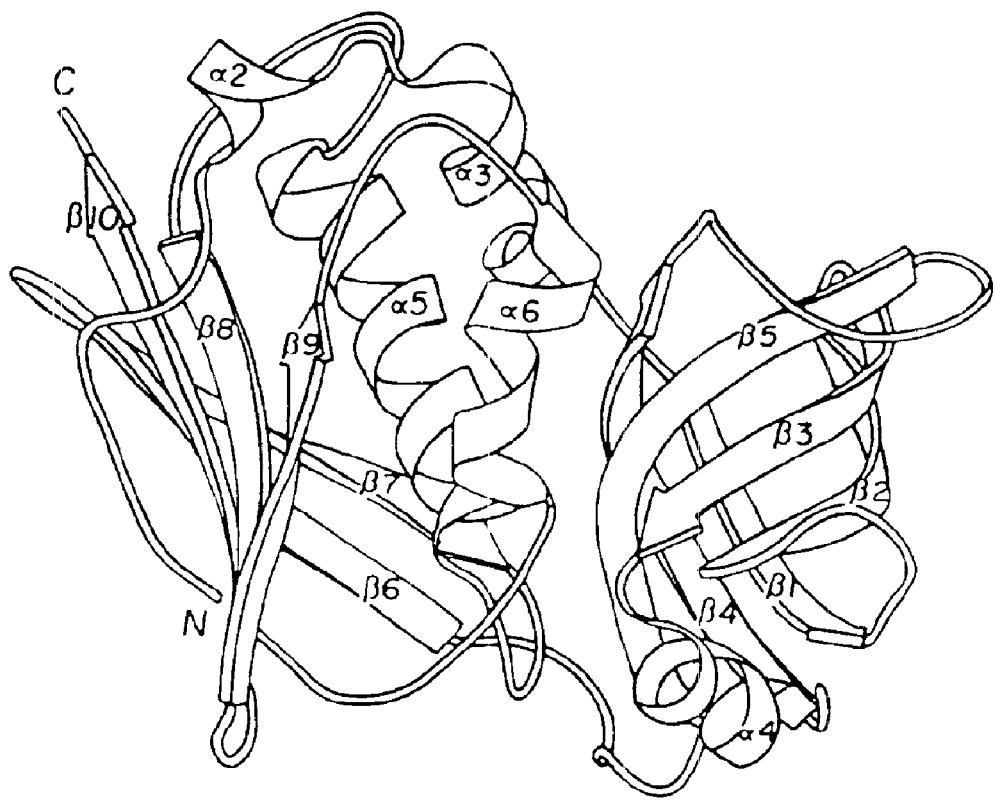
FIG. 1 Ribbon drawing of the modeled 3-dimensional structure of streptococcal pyrogenic exotoxin A. Domain A and B are indicated.

A structural model of a wild type SPE-A toxin is shown in FIG. 1. The structural model was constructed by homology modeling using Insight/Homology program available from BioSym Corp., San Diego, Calif. The model indicates that the wild type SPE-A toxin has several distinct structural features. These structural features include: helix 2 (amino acids 11–15); N-terminal alpha helix 3 (amino acids 18–26); helix 4 (amino acids 64–72); central-v helix 5 (amino acids 142–158); helix 6 (amino acids 193–202); Domain B beta strands including strand 1 (amino acids 30–36), strand 2 (amino acids 44–52), strand 3 (amino acids 55–62), strand 4 (amino acids 75–83), strand 5 (amino acids 95–106); Domain A beta strands including strand 6 (amino acids 117–126), strand 7 (amino acids 129–135), strand 8 (amino acids 169–175), strand 9 (amino acids 180–186), and strand 10 (amino acids 213–220). In addition, cysteine residues at residues 87, 90, and 98 may be important in formation of putative disulfide bonds or maintaining local 3-D conformation.

The wild type SPE-A toxin has several biological activities. These biological activities include: 1) fever; 2) STSS; 3) systemic lethality due to development of STSS or enhancement of endotoxin shock; 4) enhancing endotoxin shock; 5) induction of capillary leak and hypotension; 6) inducing release of cytokines such as IFN γ, IL-1, TNF-α and TNF-β; 7) binding to porcine aortic endothelial cells; 8) binding to MHC class II molecules; 9) binding to T-cell receptors; and 10) T-cell mitogenicity (superantigenicity). These activities can be assayed and characterized by methods known to those of skill in the art.

As used herein, the definition of a wild type SPE-A toxin includes variants of a wild type SPE-A toxin that have the same biological activity of wild type SPE-A toxin. These SPE-A toxins may have a different amino acid or their genes may have a different nucleotide sequence from that shown in FIG. 3 but do not have different biological activities. Changes in amino acid sequence are phenotypically silent. Preferably, these toxin molecules have systemic lethality and enhance endotoxin shock to the same degree as wild type SPE-A toxin shown in FIG. 3. Preferably these toxins have at least 60–99% homology with wild type SPE-A toxin amino acid sequence as shown in FIG. 3 as determined using the SS2 Alignment Algorithm as described by Altschul, S. F., *Bull. Math. Bio.* 48:603 (1986). Proteins that have these characteristics substantially correspond to a wild type SPE A.

A mutant SPE-A toxin is a toxin that has at least one change in a amino acid compared with a protein substantially corresponding to a wild type SPE-A toxin. The change can be an amino acid substitution, deletion, or addition. There can be more than one change in the amino acid sequence, preferably 1 to 6 changes. It is preferred that there are more than one change in amino acid sequence to minimize reversion of mutant SPE-A toxin to the wild type SPE-A toxin having systemic lethality or toxicity. For mutant SPE-A toxins useful in vaccines, it is preferred that the change in the amino acid sequence of the toxin does not result in a change of the toxin's ability to stimulate an antibody response that can neutralize wild type SPE-A toxin. For mutant SPE-A toxins useful in vaccines, it is especially preferred that the mutant toxins are recognized by polyclonal neutralizing antibodies to SPE-A toxin such as from Toxin Technologies in Boca Raton, Fla. or Dr. Schlievert (University of Minnesota, Minneapolis, Minn.) and that the proteolytic profile is not altered compared with wild type speA.

The changes in the amino acid sequence can be site-specific changes at one or more selected amino acid residues of a wild type SPE-A toxin. Site-specific changes are selected by identifying residues in particular domains of the molecule as described previously or at locations where cysteine residues are located. Site-specific changes at a particular location can optionally be further selected by determining whether an amino acid at a location or within a domain is identical to or has similar properties to an equivalent residue in other homologous molecules by comparison of primary sequence homology or 3-D conformation. Homologous molecules are known to those of skill in the art. A homologous molecule is one that can be identified by comparison of primary sequence homology using the SS2 alignment algorithm of Altschul et al., cited supra or a homology modelling program such as Insight/Homology from BioSym, San Diego, Calif. A homologous molecule is one that displays a significant number, typically 30–99%, of identical or conservatively changed amino acids or has a similar three dimensional structure, typically RMS error for conserved regions of <2 Angstroms, when compared to a wild type SPE-A toxin.

Changes in the amino acid sequence at a particular site can be randomly made or specific changes can be selected. Once a specific site is selected it is referred to by its amino acid number designation and by the amino acid found at that site in the wild type SPE-A as shown in FIG. 3. The amino acid number designations made in this application are by reference to the sequence in FIG. 3 with the glutamine at position 31 being counted as the first amino acid. Equivalent amino acids corresponding to those identified at a particular site in proteins substantially corresponding to a wild type SPE-A toxin may have different amino acid numbers depending on the reference sequence or if they are fragments. Equivalent residues are also those found in homologous molecules that can be identified as equivalent to amino acids in proteins substantially corresponding to a wild type SPE-A toxin either by comparison of primary amino acid structure or by comparison to a modelled structure as shown in FIG. 1 or by comparison to a known crystal structure of a homologous molecule. It is intended that the invention cover changes to equivalent amino acids at the same or similar locations regardless of their amino acid number designation.

If a specific substitution is selected for an amino acid at a specific site, the amino acid to be substituted at that location is selected to include a structural change that can affect biological activity compared with the amino acid at that location in the wild type SPE-A. The substitution may be conservative or nonconservative. Substitutions that result in a structural change that can affect biological activity include: 1) change from one type of charge to another; 2) change from charge to noncharged; 3) change in cysteine residues and formation of disulfide bonds; 4) change from hydrophobic to hydrophilic residues or hydrophilic to hydrophobic residues; 5) change in size of the amino acids; 6) change to a conformationally restrictive amino acid or analog; and 7) change to a non-naturally occurring amino acid or analog. The specific substitution selected may also depend on the location of the site selected. For example, it is preferred that amino acids in the N-terminal alpha helix have hydroxyl groups to interact with exposed amide nitrogens or that they be negatively charged to interact with the partial positive charge present at the N-terminus of the α helix.

Mutant toxins may also include random mutations targeted to a specific site or sites. Once a site is selected, mutants can be generated having each of the other 19 amino acids substituted at that site using methods such as described by Aiyar et al., *Biotechniques* 14:366 (1993) or Ho et al. *Gene* 77:51–54 (1984). In vitro mutagenesis can also be utilized to substitute each one of the other 19 amino acids or non-naturally occurring amino acids or analogs at a particular location using a method such as described by Anthony-Cahill et al., *Trends Biochem. Sci.* 14:400 (1989).

Mutant toxins also include toxins that have changes at one or more sites of the molecule not specifically selected and that have a change in amino acids that is also not specifically selected but can be any one of the other 19 amino acids or a non-naturally occurring amino acid.

Substitutions at a specific site can also include but are not limited to substitutions with non-naturally occurring amino acids such as 3-hydroxyproline, 4-hydroxyproline, homocysteine, 2-aminoadipic acid, 2-aminopimilic acid, ornithine, homoarginine, N-methyllysine, dimethyl lysine, trimethyl lysine, 2,3-diaminopropionic acid, 2,4-diaminobutryic acid, hydroxylysine, substituted phenylalanine, norleucine, norvaline, γ-valine and halogenated tyrosines. Substitutions at a specific site can also include the use of analogs which use non-peptide chemistry including but not limited to ester, ether and phosphoryl and boron linkages.

The mutant toxins can be generated using a variety of methods. Those methods include site-specific mutagenesis, mutagenesis methods using chemicals such as EMS, or sodium bisulfite or UV irradiation, by spontaneous mutation, by in vitro mutagenesis and chemical synthesis. Methods of mutagenesis can be found in Sambrook et al., A Guide to Molecular Cloning, Cold Spring Harvard, New York (1989). The especially preferred method for site-specific mutagenesis is using asymmetric PCR with three primers as described by Perrin and Gilliland, 1990. *Nucleic Acid Res.* 18:7433.

Once a mutant SPE-A toxin is generated having at least one amino acid change compared with a protein substantially corresponding to the wild type SPE-A toxin, the mutant SPE-A toxin is screened for nonlethality. It is preferred that mutant SPE-A toxins selected from this screening are substantially nonlethal in rabbits when administered using a miniosmotic pump (as described in Example 2) at the same dose or a greater dose than a wild type SPE-A toxin. A mutant SPE-A toxin or fragment thereof is substantially nonlethal if when administered to a rabbit at the same dose as the wild type toxin less than about 10–20% of rabbits die. Nonlethal mutant toxins are useful in vaccine and pharmaceutical compositions. While not meant to limit the invention, it is believed that some amino acid residues or domains that affect systemic lethality are separable from other biological activities especially T cell mitogenicity.

For mutant toxins useful in vaccine composition it is further preferred that the mutant SPE-A toxins are screened for those that can stimulate an antibody response that neutralizes wild type SPE-A toxin activity. A method for selecting mutant toxins that can stimulate an antibody response that neutralizes wild type SPE-A toxin activity is to determine whether the mutant toxin immunoreacts with polyclonal neutralizing antibodies to wild type SPE-A such as available from Toxin Technologies, Boca Raton, Fla. or Dr. Schlievert. Methods of determining whether mutant SPE-A toxins immunoreact with antibodies to wild type SPE-A toxin include ELISA, Western Blot, Double Immunodiffusion Assay and the like.

Optionally, the mutant toxins can also be screened to determine if the proteolytic profile of the mutant toxin is the same as the wild type SPE-A toxin. In some cases, it is preferred that the mutants generated do not substantially change the overall three-dimensional conformation of the mutant toxin compared with the wild type SPE-A toxin. One way of examining whether there has been a change in overall conformation is to look at immunoreactivity of antibodies to wild type SPE-A toxin and/or to examine the proteolytic profile of mutant SPE-A toxins. The proteolytic profile can be determined using such enzymes as trypsin, chymotrypsin, papain, pepsin, subtilisin and V8 protease in methods known to those of skill in the art. The proteolytic profile of wild type SPE-A with the sequence shown in FIG. 3 is known. The mutants that have a similar profile to that of wild type SPE-A are selected.

Optionally, mutant toxins can also be screened and selected to have other changes in biological activity. As described previously, there are several biological activities associated with wild type SPE-A toxin. Those biological activities include: 1) fever; 2) STSS; 4) enhancement of endotoxin shock; 5) capillary leak and hypotension; 6) inducing release of cytokines such as IFN gamma, IL-1, TNF-α and TNF-β; 7) binding to endothelial cells; 8)

binding to MHC class II molecules; 9) binding to T-cell receptors; and 10) T-cell mitogenicity (superantigenicity). These biological activities can be measured using methods known to those of skill in the art.

For mutant SPE-A toxins or fragments thereof useful in vaccine compositions, it is preferred that they are substantially nontoxic and immunoreactive with neutralizing antibodies to wild type SPE-A. Neutralizing antibodies include those that inhibit the lethality of the wild type toxin when tested in animals. Optionally, mutant SPE-A toxins can have a change in one or more other biological activities of wild type SPE-A toxin as described previously.

Optionally, preferred mutant toxins for vaccine compositions are further screened and selected for a lack of potentiation of endotoxin shock. The preferred assay for examining a lack of enhancement of endotoxin shock is described in Example 4. Rabbits preferably have no demonstrable bacterial or viral infection before testing. A lack of potentiation of or substantially no enhancement of endotoxin shock is seen when less than about 25% of the animals develop shock when the mutant SPE toxin is coadministered with endotoxin as compared to wild type SPE-A activity at the same dose. More preferably, none of the animals develop shock.

Optionally, preferred mutants for vaccine compositions also are further screened and selected for a change in T cell mitogenicity. A change in T-cell mitogenicity can be detected by measuring T-cell proliferation in a standard $^3$H thymidine assay using rabbit lymphocytes as described in Example 4; by measuring levels of production of cytokines such as IFN gamma or TNF-$\beta$; by determining the V$\beta$ type of T cell response or by determining the interaction of the molecules with MHC class II receptors. The preferred method for detecting a decrease in T-cell mitogenicity is to measure T-cell proliferation of rabbit lymphocytes in the presence and absence of the mutant toxin. Responses of T cells to wild type SPE-A toxin is greatly enhanced above a normal in vitro response to an antigen. A substantial decrease in T cell mitogenicity is seen when the mutant SPE-A toxin does not stimulate a T cell proliferative response greater than the stimulation with an antigen or negative control. Preferably, a decrease is seen such that the T cell proliferation response to the mutant SPE-A toxin is no more than two-fold above background when measured using rabbit lymphocytes at the same dose as the wild type SPE-A toxin.

Optionally, the mutant SPE-A toxins useful in vaccine is compositions are further screened and selected for a decrease in capillary leak in endothelial cells. The preferred method is using porcine aortic endothelial cells as described by Lee t el., *J. Infect. Dis.* 164:711 (1991). A decrease in capillary leak in the presence of mutant SPE-A toxins can be determined by measuring a decrease in release of a radioactively labelled compound or by a change in the transport of a radioactively labelled compound. A decrease in capillary leak is seen when the release or transport of a radioactively labelled compound is decreased to less than about two fold above background when compared with the activity of a wild type toxin.

The especially preferred mutant SPE-A toxins useful in vaccine compositions are not biologically active compared with proteins that have wild type SPE-A toxin activity. By nonbiologically active, it is meant that the mutant toxin has little or no systemic lethality, has little or no enhancement of endotoxin shock and little or no T cell mitogenicity. Preferably, the mutant SPE-A toxins selected for vaccine compositions substantially lack these biological activities, i.e., they react like a negative control or they stimulate a reaction no more than two-fold above background.

Changes in other biological activities can be detected as follows. Binding to MHC class II molecules can be detected using such methods as described by Jardetzky, *Nature* 368:711 (1994). Changes in fever can be detected by monitoring temperatures over time after administration of the mutant SPE-A toxins. Changes in the levels of cytokine production in the presence of mutant SPE-A toxins can be measured using methods such as are commercially available and are described by current protocols in immunology. (Ed. Coligan, Kruisbeck, Margulies, Shevach, and Stroker. *National Institutes of Health*, John Wiley and Sons, Inc.)

Specific examples of mutant SPE-A toxins that have at least one amino acid change and that are substantially nontoxic are described.

The especially preferred mutants for vaccine compositions are mutant SPE-A toxins that immunoreact with polyclonal neutralizing antibodies to wild type SPE-A toxin, are nontoxic, and optionally have a decrease in potentiation of endotoxin shock and a decrease in T-cell mitogenicity. The especially preferred mutants have a change in the asparagine at amino acid 20 such as the mutant N20D that has an aspartic acid substituted for asparagine at residue 20 in the mature toxin (N20D). The N20D mutant has been shown to be nontoxic, to have no enhancement of endotoxin shock and a 5-fold decrease in T cell mitogenicity. In addition, changes at amino acid 98 that result in a lack of a cysteine group at that location also result in a mutant toxin that has a decrease in enhancement in endotoxin shock and a four-fold decrease in mitogenicity. The especially preferred mutants at this location have a serine substituted for a cysteine (C98S).

The preferred mutants for stimulation of T-cell proliferation and in the treatment of cancer are those mutant toxins that are substantially nonlethal. It is preferred that these mutant toxins retain T-cell mitogenicity at least at the level of wild type SPE-A toxin. The especially preferred mutants have an amino acid change at residue 157 of the wild type SPE-A such as substitution of glutamic acid for lysine at that residue (K157E). The K157E mutant has been shown to be nonlethal but retains mitogenicity comparable to the wild type SPE-A toxin.

Mutants can be generated to affect a functional change by changing amino acids in a particular domain of a molecule as follows. A molecular model of wild type SPE-A toxin is shown in FIG. 1. The especially preferred domains include the N-terminal $\alpha$ helix 3 (amino acids 18–26), the central $\alpha$ helix 5 (amino acids 142–158), the Domain B beta strands (amino acids 30–36; 44–52; 55–62; 75 –83; and 95–106), and the Domain A beta strands (amino acids 117–126; 129–135; 169–175; 180–186; and 213–220). Cysteine residues at positions 87, 90, and 98 may also be important.

Figure 2:
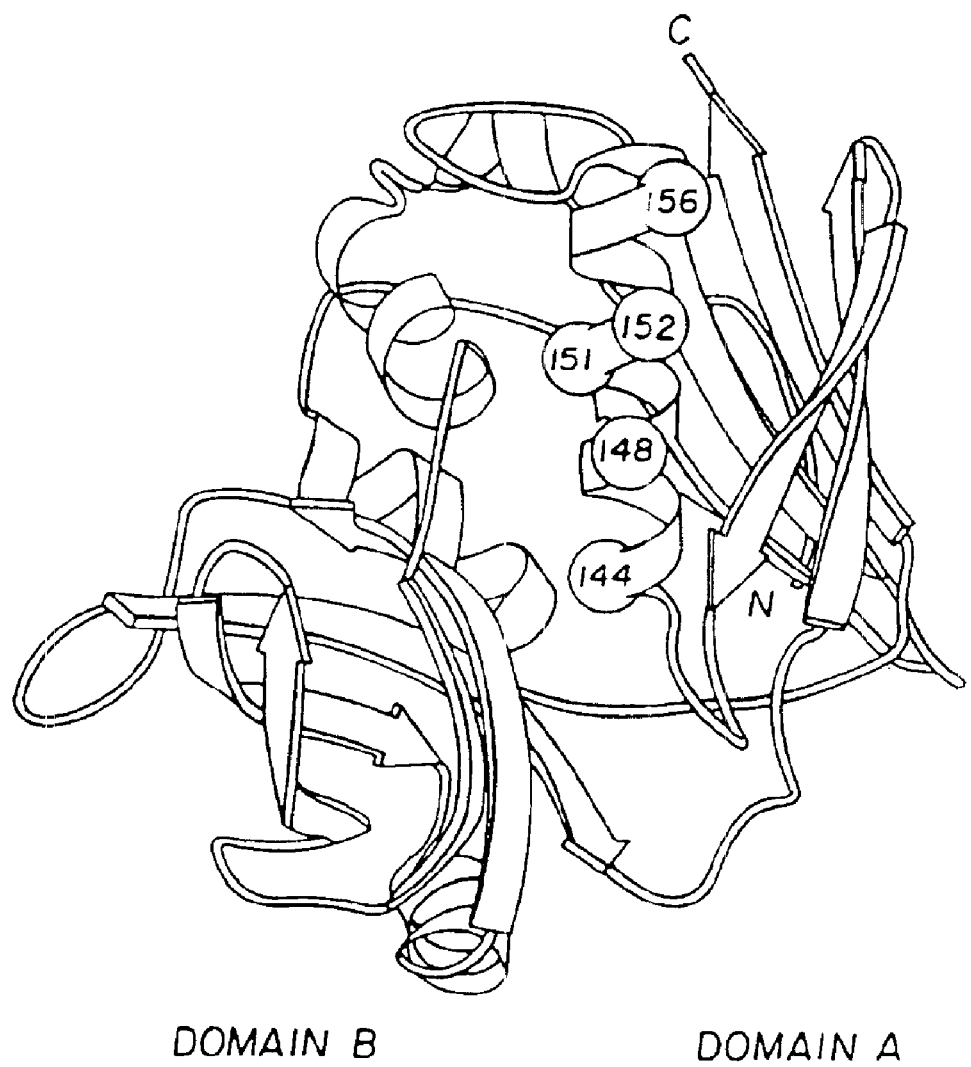
FIG. 2 View of SPE-A as seen from the back in reference to the standard view seen in FIG. 1. Numbered residues are those homologous to residues in TSST-1 evaluated for reduced systemic lethality.

While not meant to limit the invention, it is believed that these domains form specific 3-D conformations that are important in the biological functions of the wild type SPE-A activity. As can be seen in FIG. 2, the N-terminal $\alpha$ helix and central $\alpha$ helix are closely situated so that residues here may be especially important in the toxicity of wild type SPE-A molecules. In addition, amino acids in the bordering B strands that are in close proximity to the central alpha helix may also be important in toxicity. The molecular models as shown in FIGS. 1 and 2 help to identify surface residues and buried residues of the structural domains.

For vaccine compositions, changes are preferably made to the residues in N-terminal alpha helix 3 (residues 18–26) are screened and selected to decrease systemic lethality or enhancement of endotoxin or T cell mitogenicity or all three.

A specific example of a change in the N-terminal alpha helix 3 is a change in amino acid at residue 20. A change at this residue from asparagine to aspartic acid results in a decrease in enhancement of endotoxin shock, a decrease in systemic lethality, and a five-fold decrease in mitogenicity. Other changes at residue 20 are preferably those that change the distribution of charge at the surface residues or that change the interaction of the N-terminal α helix with the central α helix. Substitutions at amino acid 20 with charged amino acids such as glutamic acid, lysine, arginine are likely to have the same effect. Changes made in this region are preferably those that decrease in systemic lethality due to STSS.

Preferably, changes are also made in the central α helix 5 residues 142–158. Mutants in this region having at least one amino acid change are preferably selected for a decrease systemic lethality due to STSS. A similar central α helix identified in other toxin molecules has been shown to be associated with toxicity. A specific example is a change at residue 157. Change at this residue from lysine to glutamic acid results in a decrease in enhancement of endotoxin shock and systemic lethality due to STSS.

However, T-cell mitogenicity is not affected by a change at this residue. These results show that toxicity and enhancement of endotoxin shock are separable activities from T cell mitogenicity. For vaccine compositions, other mutant toxins with changes in this domain are optionally screened and selected for a decrease in T cell mitogenicity. A change in the type of charge present at amino acid 157 indicates that a substitution of aspartic acid for the lysine is likely to have a similar effect.

Preferably changes in domain B beta strands including residues 30–36 (beta strand 1), residues 44–52 (beta strand 2), residues 55–62 (beta strand 3), residues 75–83 (beta strand 4), and residues 95–106 (beta strand 5) (domain 5) are screened and selected for nonlethality, and optionally for a decrease in enhancement of endotoxin shock and/or T cell mitogenicity. Multiple residues that form N-terminal barrel of beta sheet in several toxins such as SEB, SEA, TSST-1 have been shown to be important for binding to MHC class II molecules. A decrease in MHC class II binding by mutant toxins can also be selected by using assays such as described by Jardetzky et al., cited supra. Changes to these residues that would disrupt beta sheet conformation or change the contact residues with MHC class II molecules, especially those on the concave surface of the beta barrel, are selected. See FIG. 1. For vaccine compositions, it is preferred that changes that may change local conformation do not change the immunoreactivity of the mutant toxins with polyclonal neutralizing antibodies to the wild type SPE-A toxin.

Preferably changes to Domain A beta strands, including residues 117–126 (domain beta strand 6), residues 129–135 (domain 7), residues 169–175 (domain 8), residues 180–186 (domain 9), and residues 213–220 (domain 10), are selected to be nonlethal, have a decrease in endotoxin shock, and/or have a decrease in T cell mitogenicity. Changes that would alter the beta sheet conformation without changing the immunoreactivity of the mutant SPE-A toxin with polyclonal neutralizing antibodies to wild type SPE-A toxin are preferably selected.

Mutant SPE-A toxins with changes to cysteine residues or introduction of disulfide bonds can be selected that have a decrease in lethality, or optionally a decrease in enhancement of endotoxin shock, and/or a decrease in T cell mitogenicity. A specific example is change at the cysteine residue 98. A change at this residue from cysteine to serine results in a mutant toxin with a decrease in mitogenicity about four-fold and a decrease in enhancement in endotoxin shock and a decrease in lethality due to STSS. Changes that eliminate the cysteine group at residue 98 can effect biological activity in a similar manner as a substitution with serine. Other changes that could be made at residue 98 include substitution of the other small aliphatic residues such as alanine, glycine or threonine. Changes at other cysteine residues at amino acid residues 90 and 97 result in a decrease in mitogenicity.

Advantageously, mutant SPE-A toxins useful in treatment methods can be generated that have more than one change in the amino acid sequence. It would be desirable to have changes at more than one location to minimize any chance of reversion to a molecule having toxicity or lethality. For vaccine compositions, it is desirable that a mutant toxin with multiple changes can still generate a protective immune response against wild type SPE-A and/or immunoreact with neutralizing polyclonal antibodies to wild type SPE-A. For pharmaceutical compositions, it is preferred that mutants with multiple changes are substantially nonlethal while maintaining mitogenicity for T cells. It is especially preferable to have about 2 to 6 changes. Examples of such mutants include those with the N20D mutation including double mutants such as N20D/K157E, N20D/C98S, triple mutants, and the like.

Double mutants of SPEA may offer advantages over single mutants. This was evaluated in three experiments detailed in Example 6. Results are provided in FIGS. 7–9. The data indicated that the N20D/C98S mutant had less toxicity than the single N20D mutant and the double mutant N20D/K157E was intermediate between the other two proteins. All three mutants were significantly less toxic than wild is type SPEA. Sera from rabbits immunized with the single and double mutants inhibited lymphocyte proliferation in response to nonmutated SPEA toxin. Lymphocyte proliferation is associated with and necessary for full toxicity of the toxin.

Animals were immunized against N20D, N20D/C98S, or N20D/K157E, as described in Example 7. Results are provided in Table 9. Animals immunized with either double mutant were completely protected from fever and enhanced susceptibility to endotoxin shock.

Triple mutants are also contemplated in this application and in one embodiment, the SPE-A mutant N20D/C98S/D45N is tested using the methods and assays of Examples 1–7 and the primers disclosed herein.

It may also be preferable to delete residues at specific sites such as deletion of amino acid residue 20 asparagine and/or deletion of amino acid 157 lysine or 98 cysteine. For vaccine compositions, mutants with deletions would be selected that immunoreact with polyclonal neutralizing antibodies to wild type SPE-A toxin and/or can stimulate a protective immune response against wild type SPE-A activity.

Mutant toxins of SPE-A are useful to form vaccine compositions. The preferred mutants for vaccine compositions have at least one amino acid change, are nontoxic systemically, and immunoreact with polyclonal neutralizing antibodies to wild type SPE-A. The especially preferred mutants include those mutant SPE-A toxins with a change at amino acid 20 such as N20D, N20D/K157E, N20D/C98S, and mutants with a deletion at residue 20 asparagine.

Mutant toxins are combined with a physiologically acceptable carrier. Physiologically acceptable diluents include physiological saline solutions, and buffered saline solutions at neutral pH such as phosphate buffered saline. Other types of physiological carriers include liposomes or polymers and the like. Optionally, the mutant toxin can be combined with an adjuvant such as Freund's incomplete adjuvant, Freund's Complete adjuvant, alum, monophosphoryl lipid A, alum phosphate or hydroxide, QS-21 and the like. Optionally, the mutant toxins or fragments thereof can be combined with immunomodulators such as interleukins, interferons and the like. Many vaccine formulations are known to those of skill in the art.

The mutant SPE-A toxin or fragment thereof is added to a vaccine formulation in an amount effective to stimulate a protective immune response in an animal to at least one biological activity of wild type SPE-A toxin. Generation of a protective immune response can be measured by the development of antibodies, preferably antibodies that neutralize the wild type SPE-A toxin. Neutralization of wild type SPE-A toxin can be measured including by inhibition of lethality due to wild type SPE-A in animals. In addition, a protective immune response can be detected by measuring a decrease in at least one biological activity of wild type SPE-A toxins such as amelioration or elimination of the symptoms of enhancement of endotoxin shock or STSS. The amounts of the mutant toxin that can form a protective immune response are about 0.1 $\mu$g to 100 mg per kg of body weight more preferably about 1 $\mu$g to about 100 $\mu$g/kg body weight. About 25 $\mu$g/kg of body weight of wild type SPE-A toxin is effective to induce protective immunity in rabbits.

The vaccine compositions are administered to animals such as rabbits, rodents, horses, and humans. The preferred animal is a human.

The mutant SPE-A toxins are also useful to form pharmaceutical compositions. The pharmaceutical compositions are useful in therapeutic situations where a stimulation of T-cell proliferation may be desirable, such as in the treatment of cancer. The preferred mutant SPE-A toxins are those that are nonlethal while maintaining T-cell mitogenicity comparable to wild type SPE-A toxin. Preferred mutants are those that have a change at residue 157 lysine of wild type SPE-A toxins such as K157E.

A pharmaceutical composition is formed by combining a mutant SPE-A toxin with a physiologically acceptable carrier such as physiological saline, buffered saline solutions at neutral pH such as phosphate buffered saline. The mutant SPE-A toxin is combined in an amount effective to stimulate T-cell proliferation comparable to wild type SPE-A toxin at the same dose. An enhancement in T-cell responsiveness can be measured using standard $^3$H thymidine assays with rabbit lymphocytes as well as by measuring T-cell populations in viva using fluorescence activated T-cell sorters or an assay such as an ELISPOT. An effective amount can also be an amount effective to ameliorate or decrease the growth of cancer cells. This can be determined by measuring the effect of the mutant SPE-A toxin on growth of cancer cells in vivo or by measuring the stimulation of cancer-specific T-cells. The range of effective amounts are 100 ng to 100 mg per kg of body weight, more preferably 1 $\mu$g to 1 mg/kg body weight. About $10^{-6}$ $\mu$g of wild type SPE-A toxin can stimulate enhanced T cell responsiveness. For example, these mutant SPE-A toxins could be used either alone or in conjunction with interleukin or interferon therapy.

The invention also includes fragments of SPE-A toxins and fragments of mutant SPE-A toxins. For vaccine compositions, fragments are preferably large enough to stimulate a protective immune response. A minimum size for a B cell epitope is about 4–7 amino acids and for a T cell epitope about 8–12 amino acids. The total size of wild type SPE-A is about 251 amino acids including the leader sequence. Fragments are peptides that are about 4 to 250 amino acids, more preferably about 10–50 amino acids.

Fragments can be a single peptide or include peptides from different locations joined together. Preferably, fragments include one or more of the domains as identified in FIG. 1 and as described previously. It is also preferred that the fragments from mutant SPE-A toxins have at least one change in amino acid sequence and more preferably 1–6 changes in amino aced sequence when compared to a protein substantially corresponding to a wild type SPE-A toxin.

Preferably, fragments are substantially nonlethal systemically. Fragments are screened and selected to have little or no toxicity in rabbits using the miniosmotic pump model at the same or greater dosage than a protein having wild type SPE-A toxin activity as described previously. It is also preferred that the fragment is nontoxic in humans when given a dose comparable to that of a wild type SPE-A toxin.

For vaccine compositions, it is preferred that the fragments include residues from the central $\alpha$ helix and/or the N-terminal $\alpha$ helix. It is especially preferred that the fragment include a change at amino acid residues equivalent to residue 20 in wild type SPE-A toxin such as N20D or a change at an amino acid residue equivalent to residue 98 cysteine in a wild type SPE-A toxin.

For vaccine compositions, it is preferable that a fragment stimulate a neutralizing antibody response to a protein having wild type SPE-A toxin activity. A fragment can be screened and selected for immunoreactivity with polyclonal neutralizing antibodies to a wild type SPE-A toxin. The fragments can also be used to immunize animals and the antibodies formed tested for neutralization of wild type SPE-A toxin.

For vaccine compositions, especially preferred fragments are further selected and screened to be nonbiologically active. By nonbiologically active, it is meant that the fragment is nonlethal systemically, induces little or no enhancement of endotoxin shock, and induces little or no T cell stimulation. Optionally, the fragment can be screened and selected to have a decrease in capillary leak effect on porcine endothelial cells.

The fragments screened and selected for vaccine compositions can be combined into vaccine formulations and utilized as described previously. Optionally, fragments can be attached to carrier molecules such as bovine serum albumin, human serum albumin, keyhole limpet hemocyanin, tetanus toxoid and the like.

For pharmaceutical compositions, it is preferred that the fragments include amino acid residues in the N-terminal Domain B $\beta$ strands 1–5 alone or in combination with the central $\alpha$ helix. It is especially preferred if the fragments include a change at an amino acid residue equivalent to the lysine at amino acid 157 of a wild type is SPE-A toxin such as K157E.

For pharmaceutical compositions, it is preferred that the fragments are screened and selected for nonlethality systemically, and optionally for little or no enhancement of endotoxin shock as described previously. It is preferred that the fragments retain T cell mitogenicity similar to the wild type SPE-A toxin. Fragments of a mutant toxin SPE-A can form pharmaceutical compositions as described previously.

Fragments of mutant SPE-A toxin can be prepared using PCR, restriction enzyme digestion and/or ligation, in vitro mutagenesis and chemical synthesis. For smaller fragments chemical synthesis may be desirable.

The fragments of mutant SPE-A toxins can be utilized in the same compositions and methods as described for mutant SPE-A toxins.

B. Methods for Using Mutant SPE-A Toxins, Vaccines Compostions or Pharmaceutical Compositions.

The mutant SPE-A toxins and/or fragments thereof are useful in methods for protecting animals against the effects of wild type SPE-A toxins, ameliorating or treating animals with STSS, inducing enhanced T-cell proliferation and responsiveness, and treating or ameliorating the symptoms of cancer.

A method for protecting animals against at least one biological activity of wild type SPE-A toxin involves the step of administering a vaccine composition to an animal to establish a protective immune response against at least one biological activity of SPE-A toxin. It is preferred that the protective immune response is neutralizing and protects against lethality or symptoms of STSS. The vaccine composition preferably includes a mutant SPE-A toxin or fragment thereof that has at least one amino acid change, that immunoreacts with polyclonal neutralizing antibodies to wild type SPE-A, and is nonlethal. The especially preferred mutant has a change at amino acid residue 20 asparagine such as the mutant N20D, or N20D/K157E or N20D/C98S.

The vaccine composition can be administered to an animal in a variety of ways including subcutaneously, intramuscularly, intravenously, intradermally, orally, intranasally, ocularly, intraperitoneally and the like. The preferred route of administration is intramuscularly.

The vaccine compositions can be administered to a variety of animals including rabbits, rodents, horses and humans. The preferred animal is a human.

The vaccine composition can be administered in a single or multiple doses until protective immunity against at least one of the biological activities of wild type SPE-A is established. Protective immunity can be detected by measuring the presence of neutralizing antibodies to the wild type SPE-A using standard methods. An effective amount is administered to establish protective immunity without causing substantial toxicity.

A mutant SPE-A toxin or fragment thereof is also useful to generate neutralizing antibodies that immunoreact with the mutant SPE-A toxin and the wild type SPE-A toxin. These antibodies could be used as a passive immune serum to treat or ameliorate the symptoms in those patients that have the symptoms of STSS. A vaccine composition as described above could be administered to an animal such as a horse or a human until a neutralizing antibody response to wild type SPE-A is generated. These neutralizing antibodies can then be harvested, purified, and utilized to treat patients exhibiting symptoms of STSS. Neutralizing antibodies to wild type SPE-A toxin can also be formed using wild type SPE-A. However, wild type SPE-A must be administered at a dose much lower than that which induces toxicity such as $1/50$ to $1/100$ of the $LD_{50}$ of wild type SPE-A in rabbits.

The neutralizing antibodies are administered to patients exhibiting symptoms of STSS such as fever, hypotension, group A streptococcal infection, myositis, fascitis, and liver damage in an amount effective to neutralize the effect of SPE-A toxin. The neutralizing antibodies can be administered intravenously, intramuscularly, intradermally, subcutaneously, and the like. The preferred route is intravenously or for localized infection, topically at the site of tissue damage with debridement. It is also preferred that the neutralizing antibody be administered in conjunction with antibiotic therapy. The neutralizing antibody can be administered until a decrease in shock or tissue damage is obtained in a single or multiple dose. The preferred amount of neutralizing antibodies typically administered is about 1 mg to 1000 mg/kg, more preferably about 50–200 mg/kg of body weight.

The mutant SPE-A toxins and/or fragments thereof are also useful in pharmaceutical compositions for stimulation of T-cell proliferation, especially in the treatment of cancer. It is especially preferred that these pharmaceutical compositions be used in the place of or in conjunction with current therapies for cancer using interleukins, interferons or tumor necrosis factors. The mutant SPE-A toxins are also useful in treating T cell lymphomas, and ovarian and uterine cancer. While not meant to limit the invention, it is believed that mutant SPE-A toxins can be selectively toxic for T lymphoma cells.

The pharmaceutical compositions include a mutant SPE-A toxin and/or fragment thereof that are nonlethal, while maintaining T cell mitogenicity. The preferred mutant SPE-A toxin is one that has a change at amino acid residue 157 lysine such as K157E.

The pharmaceutical composition is administered to a patient having cancer by intravenous, intramuscular, intradermal, orally, intraperitoneally, and subcutaneous routes, and the like. The preferred route is intravenous. The pharmaceutical composition can be administered in a single dose or multiple doses. The pharmaceutical composition is administered in an amount that is effective to stimulate enhanced T-cell proliferative response and/or to decrease the growth of the cancer without substantial toxicity. The preferred amount ranges from 100 ng to 100 mg/kg, more preferably 1 µg to 1 mg/kg. It is especially preferred that the mutant SPE-A pharmaceutical compositions are administered in conjunction with or in place of therapies using interferons, interleukins, or tumor necrosis factors.

C. DNA Expression Cassettes Encoding Mutant SPE-A Toxins and Methods of Preparation of Such DNA Expression Cassettes The invention also includes DNA sequences and expression cassettes useful in expression of mutant SPE-A toxins and/or fragments thereof. An expression cassette includes a DNA sequence encoding a mutant SPE-A toxin and/or fragment thereof with at least one amino acid change and at least one change in biological function compared to a protein substantially corresponding to a wild type SPE-A toxin operably linked to a promoter functional in a host cell. Expression cassettes are incorporated into transformation vectors and mutant SPE-A toxins are produced in transformed cells. The mutant toxins can then be purified from host cells or host cell supernatants. Transformed host cells are also useful as vaccine compositions.

Mutant SPE-A toxins or fragments thereof can also be formed by screening and selecting for spontaneous mutants in a similar manner as described for site specific or random mutagenesis. Mutant SPE-A toxins can be generated using in vitro mutagenesis or semisynthetically from fragments produced by any procedure. Finally, mutant SPE-A toxins can be generated using chemical synthesis.

DNA Sequences Encoding Mutant SPE-A Toxins

A mutant DNA sequence encoding a mutant SPE-A toxin that has at least one change in amino acid sequence can be formed by a variety of methods depending on the type of change selected. A DNA sequence encoding a protein substantially corresponding to wild type SPE-A toxin functions as template DNA used to generate DNA sequences encoding mutant SPE-A toxins. A DNA sequence encoding wild type SPE-A toxin is shown in FIG. 3 and has been deposited in a microorganism with ATTC Accession number 69830.

To make a specific change or changes at a specific location or locations it is preferred that PCR is utilized according to method of Perrin et al. cited supra. To target a change to a particular location, internal primers including the altered nucleotides coding for the amino acid change are included in a mixture also including a 5' and 31 flanking primers. A 5' flanking primer is homologous to or hybridizes to a DNA region upstream of the translation start site of the coding sequence for wild type SPE-A. Preferably, the 5' flanking region is upstream of the speA promoter and regulatory region. For example, a 5' flanking primer can be homologous to or hybridize to a region about 760 bases upstream of the translation start site as shown in FIG. 2. An example of a 5' flanking primer which includes the SPE-A promoter in upstream regulatory region has a sequence of:

```
5' GGT GGA TTC TTG AAA CAG GTG-3'    (SEQ ID NO:1)
        BamH1
```

A downstream flanking primer is homologous to or hybridizes to a region of DNA downstream of the stop codon of the coding sequence for wild type SPE-A. It is preferred that the downstream flanking primer provides for transcriptional and translational termination signals. For example, a 3' flanking primer can hybridize or be homologous to a region 200 base pairs downstream of the stop codon for the coding sequence of SPE-A. An example of a 3' flanking primer has a sequence:

```
5' CCC CCC GTC GAC GAT AAA ATA GTT GCT AAG CTA CAA GCT-3'  (SEQ ID NO:2)
            SalI
```

The upstream and downstream flanking primers are present in every PCR reaction to ensure that the resulting PCR product includes the speA promoter and upstream regulatory region and transcriptional and translation termination signals. Other upstream and downstream primers can readily be constructed by one of skill in the art. While preferred, it is not absolutely necessary that the native speA promoter and upstream regulatory region be included in the PCR product.

Each mutation at a particular site is generated using an internal primer including a DNA sequence coding for a change at a particular residue. For example, amino acid substitutions at a specific site can be generated using the following internal primers:

| Mutant | Internal Primer |
|--------|-----------------|
| N20D   | 5' AAA AAC CTT CAA GAT ATA TAT TTT CTT -3' (SEQ ID NO:3) |
| C87S   | 5'-TCC-ACA-TAA-ATA GCT GAG ATG GTA ATA-TCC-3' (SEQ ID NO:4) |
| C90S   | 5'-CTC TGT TAT TTA TCT GAA AAT GCA GAA-3' (SEQ ID NO:5) |
| C98S   | 5' CCC TCC GTA GAT CGA TGC ACT CCT TTC TGC-3' (SEQ ID NO:6) |
| K157E  | 5'-CTT ACA GAT AAT GAG CAA CTA TAT ACT-3' (SEQ ID NO:7) |
| S195A  | 5'-CCA GGA TTT ACT CAA GCT AAA TAT CTT ATG-3' (SEQ ID NO:8) |
| K16N   | 5'- CAA CTT CAC AGA TCT AGT TTA GTT AAC AAC CTT-3' (SEQ ID NO:9) (forward primer) and 5' - T TTG AAG GTT GTT AAC TAA ACT AGA TCT GTG AAG TTG-3' (backward primer) (SEQ ID NO:10) |

The underlined nucleotides indicate changes in the nucleotide sequence from a wild type speA gene as shown in FIG. 3.

Internal primers can be designed to generate a change at a specific location utilizing a DNA sequence encoding wild type SPE-A toxins such as shown in FIG. 3. Primers can be designed to encode a specific amino acid substitution at a specific location such as shown above. Primers can be designed to result in random substitution at a particular site as described by Rennell et al., J. Mol. Biol. 22:67 (1991). Primers can be designed that result in a deletion of an amino acid at a particular site. Primers can also be designed to add coding sequence for an additional amino acid at a particular location.

Primers are preferably about 15 to 50 nucleotides long, more preferably 15 to 30 nucleotides long. Primers are preferably prepared by automated synthesis. The 5' and 3' flanking primers preferably hybridize to the flanking DNA sequences encoding the coding sequence for the wild type SPE-A toxin. These flanking primers preferably include about 10 nucleotides that are 100% homologous or complementary to the flanking DNA sequences. Internal primers are not 100% complementary to DNA sequence coding for the amino acids at location because they encode a change at that location. An internal primer can have about 1 to 4 mismatches from the wild type SPE-A sequence in a primer about 15 to 30 nucleotides long. Both flanking primers and internal primers can also include additional nucleotides that encode for restriction sites and clamp sites, preferably near the end of the primer. Hybridization conditions can be modified to take into account the number of mismatches present in the primer in accord with known principles as described by Sambrook et al. Molecular Cloning—A laboratory manual, Cold Spring Harbor Laboratory Press, (1989).

More than one internal primer can be utilized if changes at more than one site are desired. For example, to generate a mutant having a change at amino acid 20 asparagine and a change at amino acid 157 lysine internal primers as shown above can be utilized in two separate reactions as described in Example S. A PCR method for generating site-specific changes at more than one location is described in Aiyar et al. cited supra. Another method is described in Example 5.

In one method, a DNA sequence encoding a mutant SPE-A toxin with one change at a particular site is generated and is then used as the template to generate a mutant DNA sequence with a change at a second site. In the first round of PCR, a first internal primer is used to generate the mutant DNA sequence with the first change. The mutant DNA sequence with the first change is then used as the template DNA and a second internal primer coding for a change at a different site is used to form a DNA sequence encoding a mutant toxin with chances in amino acid sequences at two locations. PCR methods can be utilized to generate DNA sequences with encoding amino acid sequences with about 2 to 6 changes.

The preferred PCR method is as described by Perrin et al. cited supra. Briefly, the PCR reaction conditions are: PCR is performed in a 100 ul reaction mixture containing 10 mM Tris-HCl (ph=8.3), 50 mM KCl, 1.5 mM $MgCl_2$, 200 uM each dNTP, 2 ng template plasmid DNA, 100 pmoles flanking primer, 5 pmoles internal primer, and 2.5 units of Ampli Taq DNA polymerase (Perkin Elmer Cetus). In the second amplification step, the composition of the reaction mix is as above except for equal molarity (5 pmoles each) of flanking primer and megaprimer and lug template. PCR is conducted for 30 cycles of denaturation at 94° C.×1 minute, annealing at 37° C. or 44° C.×2 minutes and elongation at 72° C. for 3 minutes.

The PCR products are isolated and then cloned into a shuttle vector (such as pMIN 164 as constructed by the method of Murray et al, *J. immunology* 152:87 (1994) and available from Dr. Schlievert, University of Minnesota, Mpls, Minn.). This vector is a chimera of *E. coli* plasmid pBR328 which carries ampicillin resistance and the staphylococcal plasmid pE194 which confers erythromycin resistance. The ligated plasmid mixtures are screened in *E. coli* for toxin production using polylconal neutralizing antibodies to wild type SPE-A from Toxin Technologies, Boca Raton, Fla. or from Dr. Schlievert. The mutant SPE-A toxins are sequenced by the method of Hsiao et al., *Nucleic Acid Res.* 19:2787 (1991) to confirm the presence of the desired mutation and absence of other mutations.

Specific DNA sequences generated in this manner include a DNA sequence that encodes mutant N20D and has the same coding sequence as shown in FIG. 3 except that an adenine at position 939 is changed to a guanine residue. A DNA sequence that encodes mutant C87S has the same coding sequence of FIG. 3 except that thymine at position 1,152 is changed to a adenine and thymine at position 1,154 is changed to cytosine. A DNA sequence that encodes mutant SPE-A toxin C98S has the same coding sequence as FIG. 3 except that guanine at position 1,185 is changed to cytosine and thymine at position 1,186 is changed to guanine. A DNA sequence that encodes mutant SPE-A toxin C90S includes a sequence that has the same coding sequence as FIG. 3 except that guanine at position 1,161 is changed to a cytosine. A DNA sequence that encodes mutant SPE-A toxin K157E includes a sequence that is the same as the coding sequence shown in FIG. 3 but is changed at position 1,351 from adenine to guanine. A DNA sequence that encodes a mutant SPE-A toxin S195A includes a DNA sequence that has the same coding sequence as shown in FIG. 3 except that thymine at position 1,464 is a quanine. A DNA sequence that encodes a mutant K16N SPE-A toxin includes a sequence that is the same as that shown in FIG. 3 except that adenine at position 941 is changed to cytosine.

It will be understood by those of skill in the art that due to the degeneracy of the genetic code a number of DNA sequences can encode the same changes in amino acids. The invention includes DNA sequences having different nucleotide sequences but that code for the same change in amino acid sequence.

For random mutagenesis at a particular site a series of primers are designed that result in substitution of each of the other 19 amino acids or a non-naturally occurring amino acid or analog at a particular site. PCR is conducted in a similar manner as described above or by the method described by Rennell et al., cited supra. PCR products are subcloned and then toxin production can be monitored by immunoreactivity with polylconal neutralizing antibodies to wild type SPE-A. The presence of a change in amino acid sequence can be verified by sequencing of the DNA sequence encoding the mutant SPE-A toxin. Preferably, mutant toxins are screened and selected for nonlethality.

Other methods of mutagenesis can also be employed to generate random mutations in the DNA sequence encoding the wild type SPE-A toxin. Random mutations or random mutagenesis as used in this context means mutations are not at a selected site and/or are not a selected change. A bacterial host cell including a DNA sequence encoding the wild type SPE-A toxin, preferably on pMIN 164, can be mutagenized using other standard methods such as chemical mutagenesis, and UV irradiation. Mutants generated in this manner can be screened for toxin production using polyclonal neutralizing antibodies to wild type SPE-A. However, further screening is necessary to identify mutant toxins that have at least one change in a biological activity, preferably that are nonlethal. Spontaneously arising mutants can also be screened for at least one change in a biological activity from wild type SPE-A.

Random mutagenesis can also be conducted using in vitro mutagenesis as described by Anthony-Cahill et al., *Trends Biochem. Sci.* 14; 400 (1989).

In addition, mutant SPE-A toxins can be formed using chemical synthesis. A method of synthesizing a protein chemically is described in Wallace, *FASEB J.* 7:505 (1993). Parts of the protein can be synthesized and then joined together using enzymes or direct chemical condensation. Using chemical synthesis would be especially useful to allow one of skill in the art to insert non-naturally occurring amino acids at desired locations. In addition, chemical synthesis would be especially useful for making fragments of mutant SPE-A toxins.

Any of the methods described herein would be useful to form fragments of mutant SPE-A toxins. In addition, fragments could be readily generated using restriction enzyme digestion and/or ligation. The pre-ferred method for generating fragments is through direct chemical synthesis for fragment of 20 amino acids or less or through genetic cloning for larger fragments.

DNA sequences encoding mutant toxins, whether site-specific or random, can be further screened for other changes in biological activity from wild type SPE-A toxin. The methods for screening for a change in at least one biological activity are described previously. Once selected DNA sequences encoding mutant SPE-A toxins are selected for at least one change in biological activity, they are utilized to form an expression cassette.

Formation of an expression cassette involves combining the DNA sequences coding for mutant SPE-A toxin with a promoter that provides for expression of a mutant SPE-A toxin in a host cell. For those mutant SPE-A toxins produced using PCR as described herein, the native speA promoter is present and provides for expression in a host cell.

Optionally, the DNA sequence can be combined with a different promoter to provide for expression in a particular type of host cell or to enhance the level of expression in a host cell. Preferably, the promoter provides for a level of expression of the mutant SPE-A toxin so that it can be detected with antibodies to SPE-A. Other promoters that can be utilized in prokaryotic cells include $P_{LAC}$, $P_{TAC}$, T7, and the like.

Once the DNA sequence encoding the mutant SPE-A toxin is combined with a suitable promoter to form an expression cassette, the expression cassette is subcloned into a suitable transformation vector. Suitable transformation vectors include at least one selectable marker gene and preferably are shuttle vectors that can be amplified in *E. coli* and gram positive microorganisms. Examples of suitable shuttle vectors include pMIN 164, and pCE 104. Other types of vectors include viral vectors such as the baculovirus vector, SV40, poxviruses such as vaccinia, adenovirus and cytomegalovirus. The preferred vector is a pMIN 164 vector, a shuttle vector that can be amplified in *E. coli* and *S. aureus*.

Once a transformation vector is formed carrying an expression cassette coding for a mutant SPE-A toxin, it is introduced into a suitable host cell that provides for expression of the mutant SPE-A toxin. Suitable host cells are cells that provide for high level of expression of the mutant toxin while minimizing the possibility of contamination with other undesirable molecules such as endotoxin and M-proteins. Suitable host cells include mammalian cells, bacterial cells such as *S. aureus*, *E. coli* and *Salmonella* spp., yeast cells, and insect cells.

Transformation methods are known to those of skill in the art and include protoplast transformation, liposome mediated transformation, calcium phosphate precipitation and electroporation. The preferred method is protoplast transformation.

Preferred transformed cells carry an expression cassette encoding a mutant SPE-A toxin with a change at amino acid 20 asparagine. Such a transformed cell has been deposited with the American Type Culture Collection in Rockville, Md. The characteristics of the deposited microorganism is that it is a *S. aureus* carrying pMIN 164 including a DNA sequence encoding mutant N20D operably linked to the native speA promoter and other regulatory regions. This microorganism was deposited in accordance with the Budapest treaty and given Accession number 69831.

Another microorganism has been deposited with the ATCC. This microorganism is *S. aureus* carrying a DNA sequence encoding the wild type SPE-A toxin operably linked to the native speA promoter and regulatory regions. This microorganism was deposited with the ATCC in accord with the Budapest treaty and given Accession number 69830.

Transformed cells are useful to produce large amounts of mutant SPE-A toxin that can be utilized in vaccine compositions. A transformed microorganism can be utilized in a live, attenuated, or heat killed vaccine. A transformed microorganism includes mutant toxin SPE-A in amounts sufficient to stimulate a protective immune response to wild type SPE-A. Preferably, the mutant SPE-A toxin is secreted. The microorganism is preferably nonpathogenic to humans and includes a mutant toxin with multiple amino acid changes to minimize reversion to a toxic form. The microorganism would be administered either as a live or heat killed vaccine in accordance with known principles. Preferred microorganisms for live vaccines are transformed cells such as *Salmonella* spp.

A viral vector including an expression cassette with a DNA sequence encoding a mutant SPE-A toxin or fragment thereof operably linked to a promoter functional in a host cell can also be utilized in a vaccine composition as described herein. Preferably, the promoter is functional in a mammalian cell. An example of a suitable viral vector includes pox viruses such as vaccinia virus, adenoviruses, cytomegaloviruses and the like. Vaccinia virus vectors could be utilized to immunize humans against at least one biological activity of a wild type SPE-A toxin.

The invention also includes a vaccine composition comprising an nucleic acid sequence encoding a mutant SPE-A toxin or fragment thereof operably linked to a promoter functional in a host cell. The promoter is preferably functional in a mammalian host cell. The nucleic acid sequence can be DNA or RNA. The vaccine composition is delivered to a host cell or individual for expression of the mutant SPE A toxin or fragment thereof within the individuals own cells. Expression of nucleic acid sequences of the mutant SPE A toxin or fragment thereof in the individual provides for a protective immune response against the wild type SPE A toxin. Optionally, the expression cassette can be incorporated into a vector. A nucleic acid molecule can be administered either directly or in a viral vector. The vaccine composition can also optionally include a delivery agent that provides for delivery of the vaccine intracellularly such as liposomes and the like. The vaccine composition can also optionally include adjuvants or other immunomodulatory compounds, and additional compounds that enhance the uptake of nucleic acids into cells. The vaccine composition can be administered by a variety of routes including parenteral routes such as intravenously, intraperitoneally, or by contact with mucosal surfaces.

Conditions for large scale growth and production of mutant SPE-A toxin are known to those of skill in the art. A method for purification of mutant SPE-A toxins from microbial sources is as follows. *S. aureus* carrying the mutant or the wild type speAs in pMIN164 are grown at 37° C. with aeration to stationary phase in dialyzable beef heart medium, containing 5 $\mu$g/ml of erythromycin. Cultures are precipitated with four volumes of ethanol and proteins resolubilized in pyrogen free water. The crude preparations are subjected to successive flat bed isoelectric focusing separations in pH gradients of 3.5 to 10 and 4 to 6. The fractions that are positive for toxin by antibody reactivity are extensively dialyzed against pyrogen free water, and an aliquot of each is tested for purity by SDS polyacrylamide gel electrophoresis in 15% (weight/volume) gels. Polyclonal neutralizing antibodies to SPE-A are available from Toxin Technologies, Boca Raton, Fla. or Dr. Schlievert. Other methods of purification including column chromatography or HPLC can be utilized.

This invention can be better understood by way of the following examples which are representative of the preferred embodiments thereof, but which are not to be construed as limiting the scope of the invention.

EXAMPLE 1

Cloning and Expression of SPE-A Wild Type

The gene encoding wild type SPE-A toxin (speA) was cloned from *E. coli* as described in Johnson et al., *Mol. Gen. Genet.* 194:52–56 (1984). Briefly, the speA gene was identified by cloning of a HindIII digest of Phage T12 DNA in pBR322 in *E. Coli* RR1. Transformants were selected by identifying those positive for toxin production using polylconal neutralizing antisera to A toxin. A nucleotide sequence for A toxin is reported in Weeks et al, *Inf.* 1 mm. 52: 144 (1986).

A DNA sequence including the speA gene was subcloned and then expressed in *S. aureus*. The speA carried on a *E. coli* plasmid was digested with restriction enzymes HindIII and SalI. The fragments were purified and ligated into HindIII-SalI sites of pMIN 164 (available as described previously). The vector pMIN 164 is a chimera of the staphylococcal plasmid pE194 (carrying erythromycin resistance) and the *E. coli* vector pBR328 (carrying Amp and resistance). Cloning of speA into the HindIII-SalI sites of this vector disrupts Tet resistance. The promoter present in this plasmid immediately upstream of the cloned gene is the native speA promoter.

Expression of the speA gene was verified by detecting the toxin in a double immunodiffusion assay with polyclonal neutralizing antibodies to SPE-A from Toxin prepared in the inventors laboratory.

EXAMPLE 2

Administration and Immunization of Rabbits with Recombinantly Produced SPE-A (wt)

Administration of recombinantly produced SPE-A to animals induces STSS. Immunization of animals with recombinantly produced SPE-A reduces the death rate when animals are challenged with M3 or M1 streptococci and protects animals against STSS.

Administration of SPE-A induces STSS in rabbits. A rabbit model for STSS has been established by administration of SPE-A in subcutaneously implanted miniosmotic pumps. Lee et al., *Infect Immun.* 59:879 (1991). These pumps are designed to release a constant amount of toxin over a 7-day period, thus providing continuous exposure to the toxin. Recombinantly produced SPE-A was administered to rabbits at a total dose of 200 μg/in 0.2 ml over a 7-day period. The results indicate that animals treated with SPE-A developed the criteria of STSS with nearly all animals succumbing in the 7-day period (data not shown). The symptoms of STSS in rabbits include weight loss, diarrhea, mottled face, fever, red conjunctiva and mucosa, and clear brown urine. As expected, control non-toxin treated animals remained healthy. Two other major observations were made: 1) fluid replacement provided complete protection to the animals as expected, and 2) none of the toxin treated animals developed necrotizing fascitis and myositis, indicating factors other than, or in addition to, SPE-A are required for the soft tissue damage.

Development of the clinical features of STSS correlates with administration of SPE-A. Rabbits injected with SPE-A positive streptococci developed STSS whereas those injected with SPE-A negative streptococci did not show symptoms of STSS.

It is well known that SPE-A is a variable trait made by some group A streptococci. The gene for SPE-A is encoded by bacteriophage T12, and well-characterized streptococcal strains were established that differ only in whether or not the SPE-A phage, referred to as T12 phage, is present. Streptococcal strain $T25_3$ cured T12 is positive for production of SPE-A, whereas $T25_3$ cured is SPE-A negative.

Rabbits were injected subcutaneously with SPE-A positive streptococci $T25_3$ cured T12 or SPE-A negative $T25_3$ cured into implanted Wiffle golf balls, as described by Scott et al., *Infect Immunity* 39:383 (1983). The results are shown in Table 1. The results show that animals injected with SPE-A positive streptococci developed the clinical features of STSS, and 6/8 succumbed. The two surviving animals developed antibodies to SPE-A. In contrast, the toxin negative strain, $T25_3$ cured, induced only fever, and no deaths were observed, even at much higher bacterial cell concentrations. As in the previous animal model experiments, no evidence of soft tissue necrosis was observed. Furthermore, the streptococci remained localized in the golf balls, suggesting these streptococcal strains were not highly invasive.

TABLE 1

Induction of STSS by speA in a Wiffle ball Rabbit Model

| Treatment | Average Highest Temperature (° C.) | Dead/Total |
|---|---|---|
| None | 39.1 | 0/4 |
| $T25_3$ cured T12* | 41.2 | 6/8‡ |
| $T25_3$ cured⁺ | 40.7 | 0/6 |
| $T25_3$ cured⁺ | 41.0 | 0/6 |

*Approximately $1 \times 10^8$ cells
⁺Approximately $1 \times 10^{11}$ cells
‡2 survivors developed antibodies to SPE-A Immunization with recombinantly produced SPE-A decreased death rates when rabbits were challenged with M1 or M3 streptococci. Rabbits were immunized with cloned SPE-A derived from *S. aureus* to prevent the possibility of immunizing the animals with contaminating streptococcal products, such as M protein. Control animals were not immunized against SPE-A. The rabbits received 50 μg of recombinantly produced SPE-A in emulsified in Freund's incomplete adjuvant subcutaneously. After 9 days, rabbits were challenged subcutaneously with 25 ml of M3 ($1.4\times10^9$ total CFU) or M1 ($4.2\times10^9$ total CFU) streptococci grown in dialyzed beef heart medium. The M1 and M3 streptococcal isolates are clinical isolates. The M1 isolate is designated MNST and the M3 isolate is designated MNBY. These isolates are available from Dr. Schlievert, University of Minnesota, Mpls. Minn.

The data presented in Table 2 show the striking results of these experiments.

TABLE 2

Protection of Rabbits from STSS with necrotizing *fascitis* and *myositis*, induced by M3 or M1 *streptococci*, by prior immunization against SPE-A

| Number of Animals | Immunizing Agent* | Challenge Agent⁺ | Number Alive‡ / Total | |
|---|---|---|---|---|
| 20 | — | M3 | 4/20 | P << 0.001§ |
| 20 | SPE-A | M3 | 16/19 | |
| 17 | — | M1 | 9/17 | P < 0.04§ |
| 15 | SPE-A | M1 | 13/15 | |

*Animals were immunized against cloned SPE-A prepared from *S. aureus*; ELISA titers against SPE-A were greater than 10,000.
⁺Animals were challenged subcutaneously with $1.4 \times 10^9$ CFU M3 or $4.2 \times 10^9$ CFU M1 *streptococci* in a dialyzable beef heart medium.
‡According to the guidelines of the University of Minnesota Animal Care Committee, the experiment which used M3 *streptococci* was terminated after 24 h, and the experiment that used M1 *streptococci* was terminated after 48 h.
§P values determined by Fisher's Exact Probability Test.

As indicated 16 of 19 SPE-A immunized rabbits survived challenge with M3 streptococci, whereas only 4 of 20 nonimmune animals survived. The surviving immune animals showed clear evidence of contained soft abscess formation, upon which examination of the fluid, was filled with PMNs. Similar results were obtained in studies of M1 streptococci, except the M1 organisms were not as virulent as the M3 organisms (Table 2). Higher numbers of M1 streptococci were used, and a reduced death rate in the rabbits was seen, even in nonimmune control animals. This may reflect the approximately 50-fold lower SPE-A production by M1 strains compared to M3 strains.

In contrast, none of the nonimmune animals showed abscess formation, and examination of fluid from 2/2 animals revealed no PMN infiltrate. These results show that one major difference between the SPE-A immune versus nonimmune animals appears to be whether or not an inflammatory response could be mounted. Prior work showed that SPE-A, as well as other pyrogenic toxin superantigens, induce macrophages to produce high levels of TNF-α. TNF-α greatly reduces PMN chemotaxis, apparently through down regulation of chemotactic receptors. Therefore, it is believed that the results show that antibodies in the SPE-A immunized animals (titers>10,000 by ELISA) block the release of TNF-α from macrophages by neutralizing SPE-A, thus allowing the development of a protective inflammatory response. In the nonimmune animals SPE-A could cause a significant release of TNF-α which in turn prevents development of a protective chemotactic response.

It is important to note that all of the animals that died except one showed extensive soft tissue damage as evidenced by their entire sides turning purple-black and in many cases sloughing. One animal in the immunized group died after immunization. The lack of detectable inflammation in the tissue of these animals suggest that streptococcal factors and not components of a host immune response causes necrotizing fascitis and myositis. Other extracellular factors may also contribute to the soft tissue damage, such as SPE B and streptolysins O and S.

All of the above data make a strong case for the causative role of pyrogenic toxin superantigens, and particularly SPE-A, when present, in the development of STSS.

EXAMPLE 3

Site Directed Mutagenesis of a DNA Sequence Encoding SPE-A

Locations in the SPE-A molecule important for biological activity were identified using site directed mutagenesis. Single amino acid changes were introduced into various regions of the molecule as described below.

The model of the three dimensional structure of SPE-A is shown in FIG. 1. This model structure was constructed by Homology using an Insight/Homology program from Bio-Sym Corp., San Diego, Calif. This molecule has several domains identified as:

| Domain | Corresponding Amino Acids |
|---|---|
| Helix 2 | 11–15 |
| N terminal α-helix, helix 3 | 18–26 |
| Domain B - β strands | |
| strand 1 | 30–36 |
| strand 2 | 44–52 |
| strand 3 | 55–62 |
| strand 4 | 75–83 |
| strand 5 | 95–106 |
| Central α-helix, helix 5 | 142–158 |
| Domain A - β strands | |
| strand 6 | 117–126 |
| strand 7 | 129–135 |
| strand 8 | 169–175 |
| strand 9 | 180–186 |
| stand 10 | 213–220 |
| Helix 4 | 64–72 |
| Helix 6 | 193–202 |

Amino acid number designations are made by reference to the sequence in FIG. 3.

Amino acids were selected in each of the domains and to alter the cysteine residues in the molecule. The especially preferred regions are the N terminal α-helix (18–26); the central α-helix (142 to 158); Domain A β strands and Domain B β strands.

Target residues for mutagenesis were chosen among the conserved amino acids throughout the pyrogenic toxin family by comparing primary amino acid sequence and/or 3-D conformational similarities or homologies using computer programs as described previously. The changes made to each of the amino acids were selected to change the characteristics of the amino acid side chain of residue at the particular site. For example, at three of the residues (87, 90 and 98) serine was substituted for cysteine so as to alter the sulphydryl groups in the molecule. At three other amino acid residues changes were made in the charge present at that site.

For example, a lysine was changed to a glutamic (157) acid, lysine was changed to asparagine (16) and asparagine was changed to aspartic acid (20).

Other amino acids may affect the interaction of the toxins with MHC Class II molecules. In another molecule, the TSST-1 N terminal β barrel strands were important for contacts with α and β chains of MHC class II molecules. Therefore, changes in the Domain A and Domain B β strands may be important for controlling the interaction of these molecules with MHC Class II molecules. In addition, changes in the residues can be prepared using random mutagenesis and substitution of each of the other 19 amino acids at a particular location and then selecting those mutants showing an alteration in biological activity such as lethality.

The mutant SPE-A molecules were prepared using site directed mutagenesis using polymerase chain reaction (PCR) in which the template DNA was the cloned SPE-A gene from phage T12. These primers were utilized for each mutation generated. Generation of each mutant involved using three primers as follows: an upstream 5' flanking primer, an internal primer including the change in DNA sequence coding for a change in an amino acid and a downstream flanking primer. The upstream flanking primer was included in every PCR reaction and is homologous to a DNA region about 760 bases upstream of the translational start site and has a sequence:

```
5' GGT GGA TCC TTG AAA CAG GTG CA-3' (SEQ ID NO:11)
        BamH1
```

The resulting PCR product includes the speA promoter and possible upstream regulatory region. The downstream flanking primer is complementary to a region of DNA about 270 bases downstream of the stop codon and has a sequence:

```
5'-CCC CCC GTC GAC GAT AAA ATA GTT GCT AAG CTA CAA GCT-3'   (SEQ ID NO:2)
           Sal I
```

The downstream flanking primer is present in every PCR reaction and because of the location of the primer the PCR product contains a putative transcription termination sequence.

Each mutation is generated using an internal primer including a DNA sequence coding for a change at a particular amino acid residue. The internal primers used to generate each mutant are as follows:

| Mutant | Internal Primer |
|---|---|
| N20D | 5' AAA AAC CTT CAA GAT ATA TAT TTT CTT -3' (SEQ ID NO:3) |
| C87S | 5'-TCC-ACA-TAA-ATA GCT GAG ATG GTA ATA-TCC-3' (SEQ ID NO:4) |
| C90S | 5'-CTC TGT TAT TTA TCT GAA AAT GCA GAA-3' (SEQ ID NO:5) |

-continued

| Mutant | Internal Primer |
|---|---|
| C98S | 5' CCC TCC GTA GAT C̲G̲A TGC ACT CCT TTC TGC-3' (SEQ ID NO:6) |
| K157E | 5'-CTT-ACA-GAT-AAT-G̲AG-CAA-CTA TAT ACT-3' (SEQ ID NO:7) |
| S195A | 5'-CCA GGA TTT ACT CAA G̲CT AAA TAT CTT ATG-3' (SEQ ID NO:8) |
| K16N | 5'- CAA CTT CAC AGA TCT AGT TTA GTT AAC̲ AAC CTT-3' (SEQ ID NO:9) (forward primer) and 5' - T TTG AAG GTT G̲TT AAC TAA ACT AGA TCT GTG AAG TTG-3' (SEQ ID NO:10) (backward primer) |

The underlined residues indicate changes in coding sequence made from DNA sequence coding will type SPE-A.

PCR was conducted as follows: Briefly, a downstream flanking primer and a forward primer spanning the site of mutation and containing the nucleotide substitutions necessary to generate an amino acid change were mixed in unequal molarity in a standard PCR reaction. The DNA product obtained was prevalent in the strand containing the mutation. This product, or megaprimer, that can be several hundred bases long, was isolated by electrophoresis in 1% agarose gel and eluted by the use of the Geneclean kit, as recommended by the manufacture (Bio 101, La Jolla, Calif.).

Briefly, the PCR reaction conditions are: PCR is performed in a 100 ul reaction mixture containing 10 mM Tris-HCl (ph=8.3), 50 mM KCl, 1.5 mM $MgCl_2$, 200 uM each dNTP, 2 ng template plasmid DNA, 100 pmoles flanking primer, 5 pmoles internal primer, and 2.5 units of Ampli Taq DNA polymerase (Perkin Elmer Cetus). In the second amplification step, the composition of the reaction mix is as above except for equal molarity (5 pmoles each) of flanking primer and megaprimer and 1 ug template. PCR is conducted for 30 cycles of denaturation at 94° C.×1 minute, annealing at 37° C. or 44° C.×2 minutes and elongation at 72° C. for 3 minutes. Hybridization conditions can be varied in accord with known principles depending on the primer size, mismatches, and GC content.

A plasmid containing the speA cloned gene and flanking sequences was used as a template. In the second step, the megaprimer and an upstream flanking primer were combined in the reaction mixture in equal molarity to generate the full length mutant speA.

The mutant speAs were digested with appropriate restriction enzymes and cloned into the shuttle vector pMIN 164 This vector is a chimera of the *E. coli* plasmid pBR328, which carries an ampicillin resistance gene, and the staphylococcal plasmid pE194, which confers erythromycin resistance. The ligated plasmid mixtures were transformed, selected for, and screened in *E. coli*. Clones positive for toxin production, as judged by double immunodiffusion assays, were sequenced by the method of Hsiao cited supra to confirm the presence of the desired mutation and the absence of other mutations. Plasmids were then transformed in *S. aureus* strain RN 4220 (available from Richard Novick, Skirball Institute, New York, N.Y.) for expression and production of mutant toxins.

*S. aureus* carrying the mutant or the wild type speAs in pMIN164 were grown at 37° C. with aeration to stationary phase in dialyzable beef heart medium, containing 5 µg/ml of erythromycin. Cultures were precipitated with four volumes of ethanol and proteins resolubilized in pyrogen free water. The crude preparations were subjected to successive flat bed isoelectric focusing separations in pH gradients of 3.5 to 10 and 4 to 6. The fractions that were positive for toxin by antibody reactivity were extensively dialyzed against pyrogen free water, and an aliquot of each was tested for purity by SDS polyacrylamide gel electrophoresis in 15% (weight/volume) gels (data not shown). All mutants prepared were as resistant as the native toxin to treatment for 60 minutes with trypsin (2 µg/µg SPE-A), and this together with the conserved reactivity to polyclonal antibodies raised against native SPE-A indicates that the mutations introduced do not cause gross structural changes of the toxin. Using these methods, 7 mutants having single amino acid substitutions in the amino acid sequence of SPE-A were generated.

EXAMPLE 4

Biological Activity Profile of Mutant SPE-A

Biological activities of the mutant toxins were evaluated and compared to those of the wild type SPE-A. The mutant toxins were tested for the ability to stimulate proliferation of T lymphocytes (superantigenicity), to enhance host susceptibility to endotoxin shock and for development of toxic shock syndrome and lethality.

The ability to stimulate proliferation of T lymphocytes was measured as [$^3$H] thymidine incorporation into cellular DNA of rabbit splenocytes. A standard 4-day mitogenicity assay was performed in 96 well microtiter plates. Each well contained $2\times10^5$ rabbit splenocytes resuspended in 200 µl RPMI 1640 (Gibco, Grand Island, N.Y.) supplemented with 25 mM HEPES, 2.0 mM L-glutamine, 100 U penicillin, 100 µg/ml streptomycin and 2% heat inactivated FCS. 20 µl samples of exotoxins were added in quadruplicate amounts in final amounts: 1 µg to $10^{-5}$ µg/well. The background cellular proliferation was determined in quadruplicate wells by adding 20 µl RPMI to the splenocytes. After 3 days of incubation in a humidified chamber at 37° C. and 7% $CO_2$, 1.0 µCi (20 µl volume of 5-[methyl-$^3$H]-thymidine (46 Ci/mmole, Amersham, Arlington Heights, Ill.) was added to each well and incubated for 18 hours. Cellular DNA was collected on glass fiber filters and the [methyl-$^3$H] thymidine incorporation was quantified by liquid scintillation counting. Three separate assays using three different rabbit donors were performed. Exoprotein concentrations were tested in quadruplicate in each of three assays. Results are presented as CPM.

The ability to enhance host susceptibility to endotoxin shock was tested in American Dutch Belted rabbits. Animals weighing between 1 and 2 kg were injected in the marginal ear vein with 5 µg/kg body weight of SPE-A (equal to ⅟₅₀ $LD_{50}$) and challenged 4 hours later by IV injection of 1 or 10 µg/kg body weight of endotoxin (about ⅟₁₀₀ $LD_{50}$) from *Salmonella typhimurium*. Control rabbits received injections with PBS. The animals were monitored after 48 hours for death.

Lethality was also measured using miniosmotic pumps implanted subcutaneously in American Dutch Belted rabbits and containing 200 µg of toxin. Individual proteins (200 µg) were injected in 0.2 ml PBS into miniosmotic pumps (Alzet, AlzaCo. Palo Alto, Calif.). The pump is designed to deliver a constant amount of toxin over a 7-day period. Rabbits were monitored 3 times daily for signs of toxic shock syndrome such as diarrhea, erythema of conjunctivae and ears, shock and death for up to 8 days.

Figure 4A:
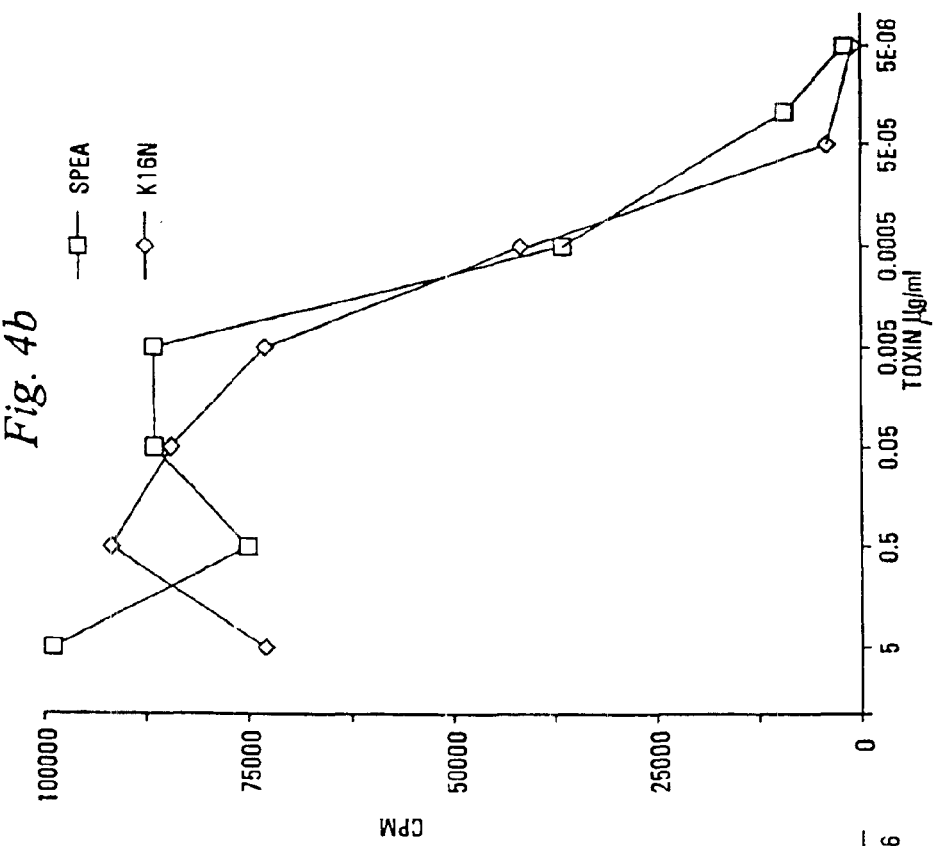
FIGS. 4A and 4B T cell proliferation assay. Rabbit splenocytes were incubated in 96 well microtiter plates in quadruplicate with SPE-A, K16N-SPE-A, and N20D-SPE-A for 72 hours. Cells were pulsed with [$^3$H] thymidine for 18 to 24 hours, harvested onto filters, and [$^3$H] thymidine incorporation was measured in a scintillation counter. Results are expressed as counts per minute (CPM) versus concentrations of toxin in μg/ml. Data presented are from the most representative of three independent experiments.
Figure 4B:
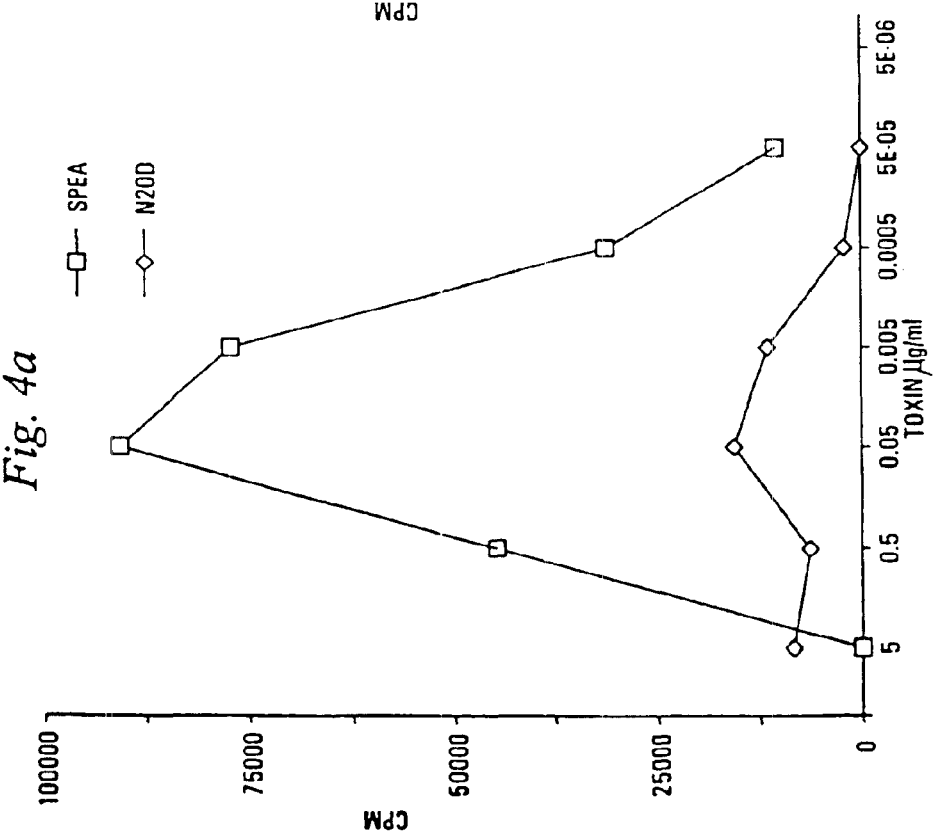
Figure 6A:
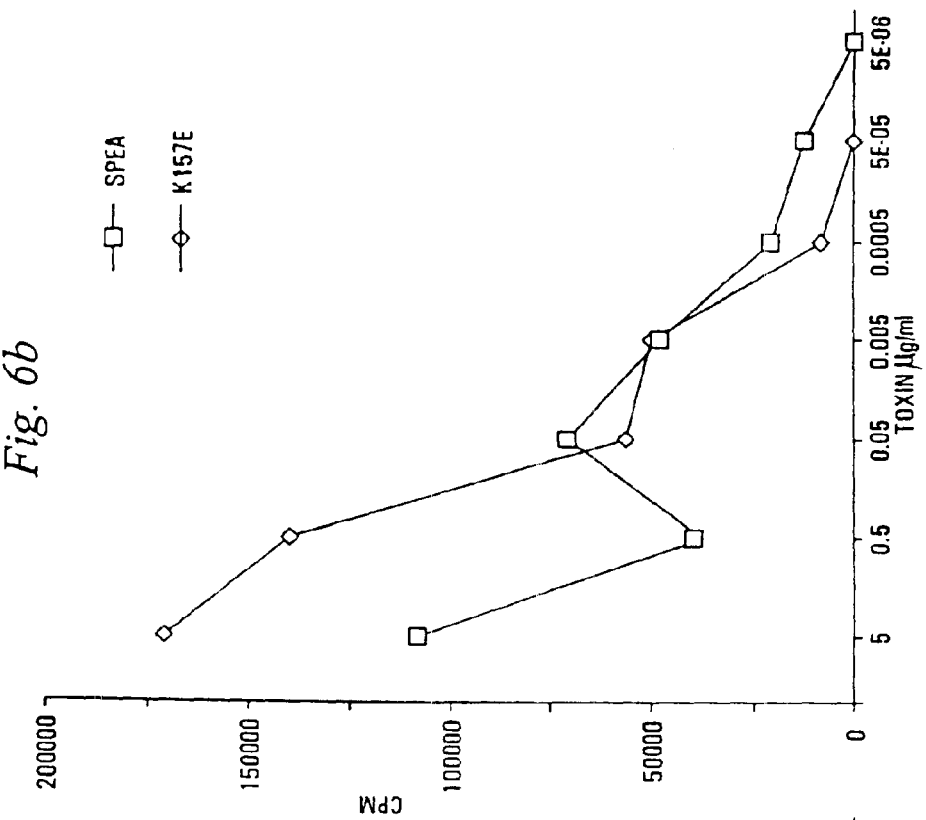
FIGS. 6A and 6B T cell proliferation assay. Rabbit splenocytes were incubated in 96 well microtiter plates in quadruplicate with SPE-A, K157E-SPE-A, and S195A-SPE-A for 72 hours. Cells were pulsed with [$^3$H] thymidine for 18 to 24 hours, harvested onto filters, and [$^3$H]thymidine incorporation was measured in a scintillation counter. Results are expressed as counts per minute (CPM) versus concentrations of toxin in μg/ml. Data presented and from the more representative of three independent experiments.
Figure 6B:
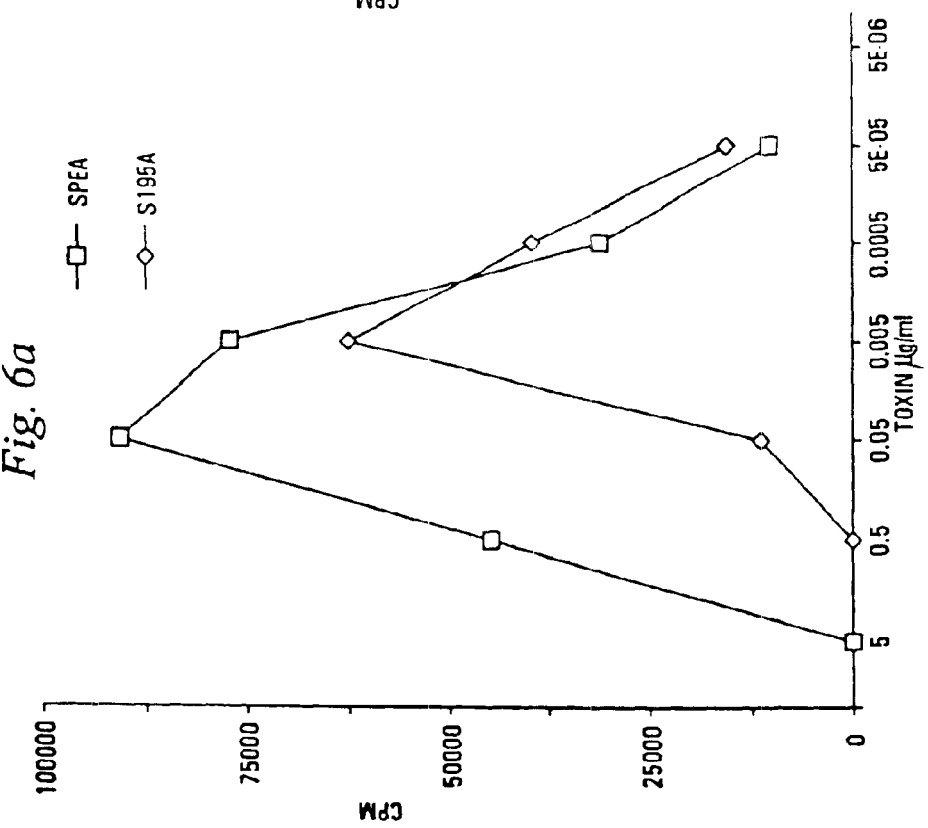

The results of the T cell mitogenicity studies are shown in FIGS. 4, 5 and 6. The results show that the mutant N20D had a five-fold decrease in superantigenicity or T cell mitogenicity activity. Mutants C87S and C98S also had a 4-fold decrease in mitogenicity for T cells. Thus, several of the mutations affected biological activity of superantigenicity or T cell mitogenicity.

The results of enhancement of endotoxin shock and lethality are shown in Tables 3, 4, and 5 shown below.

TABLE 3

Mutants SPE-A-K16N and SPE-A-N20D assayed for ability to cause endotoxin enhancement or lethality when administered in subcutaneous miniosmotic pumps. Results are expressed as ratio of deaths over total rabbits tested

|  | Protein | | |
| --- | --- | --- | --- |
|  | SPE-A | K16N | N20D |
| Endotoxin enhancement (1 µg/kg endotoxin) | 3/3 | 6/7 | 0/3 |
| Lethality in miniosmotic pumps | 3/4 | ND | 0/4 |

TABLE 4

Mutants SPE-A-C87S, SPE-A-C90S, and SPE-A-C98S tested for ability to induce endotoxin enhancement or lethality when administered in subcutaneous miniosmotic pumps. Results are expressed as ratio of deaths over total number of treated rabbits.

|  | Protein | | | |
| --- | --- | --- | --- | --- |
|  | SPE-A | C87S | C98S | C90S |
| Endotoxin enhancement 1 µg/kg body weight | 2/3 | 1/3 | 0/3 | ND |
| Endotoxin enhancement 10 µg/kg body weight | 2/3 | 3/3 | 1/3 | ND |
| Lethality in miniosmotic pumps | 3/4 | ND | ND | 3/3 |

TABLE 5

Mutants SPE-A-K157E and SPE-A-S195A tested for ability to induce lethality when administered in subcutaneous miniosmotic pumps. Results are expressed as ratio of deaths over total number of treated rabbits

|  | Protein | | |
| --- | --- | --- | --- |
|  | SPE-A | K157E | S195A |
| Lethality in miniosmotic pumps | 6/8 | 0/4 | 3/3 |

The results show that animals treated with the mutant N20D did not develop STSS when tested using either model of STSS. The mutation in N20D is located in an organized α-helix bordering the deep groove on the back of the toxin (FIG. 1). This residue is important both in superantigenicity and lethality functions of the molecule.

Mutations that eliminated sulphydryl groups and, therefore, that interfere with possible disulfide linkages, have varied effects on the biological activities of SPE-A, depending on which cysteine residue was mutated. The C90S mutant remained completely lethal (Table 4), and T cell stimulatory activity was not significantly decreased (FIG. 5a). In contrast, C87S and C98S mutations reduced approximately four fold the toxin's mitogenicity (FIG. 5b). However, ability to cause endotoxin shock was affected differently by the two mutations, with C98S being only weakly toxic, but C87S being strongly toxic (Table 4). An explanation for these results is based upon the relative positions of the three cysteine residues in the primary sequence and in the 3-dimensional structure (FIG. 1). The lack of the sulfhydryl group of C98 may preclude formation of a putative disulfide bridge seen in staphylococcal enterotoxins, and therefore, the conformation of the loop would be lost. This would have detrimental effects for the activity if amino acids in this loop are responsible for contact with host cellular receptors or have some other function in biological activity of the molecule. In the case of C87S mutation, the putative disulfide bond could still be created between C90 and C98, preserving most of the conformation and, therefore, the activity.

Mutant K157E, located within the long central α-helix, retained complete superantigenicity (FIG. 6b), but was non-lethal when administered in miniosmotic pumps to rabbits (Table 6).

Residue S195A, which is part of α-5 helix, may not be important for the biological activities tested, since its mutation does not affect activities tested thus far. This residue may not be exposed to the environment or may not contribute to binding.

These results show that lethality and superantigenicity can be affected by mutations at several sites. Lethality can be affected by mutations in residues in the N terminal α-helix (N20D) and in the central α-helix (K157E). Mitogenicity can be affected by mutations in the N terminal α-helix and changes to sulfhydryl groups.

These results also show that mitogenicity and lethality are separable activities as mutants were generated that affect lethality without affecting superantigenicity (K157E) and that affected mitogenicity without affecting lethality (C87S).

EXAMPLE 5

Preparation of Double or Triple Mutants of SPE-A Using PCR

There are a number of methods that can be used to generate double or triple mutant SPE-A toxins or fragments thereof.

Mutant SPE-A toxins with two or more changes in amino acid sequences can be prepared using PCR as described previously. In a first PCR reaction, an first internal primer coding for the first change at a selected site is combined with 5 and 3' flanking primers to form a first PCR product. The first PCR product is a DNA sequence coding for a mutant SPE-A toxin having one change in amino acid sequence. This first PCR product then serves as the template DNA to generate a second PCR product with two changes in amino acid sequence compared with a protein having wild type SPE-A activity. The first PCR product is the template DNA combined with a second internal primer coding for a change in amino acid at a second site. The second internal primer is also combined with the 5' and 3' flanking primers to form a second PCR product. The second PCR product is a DNA sequence encoding a mutant SPE-A toxin with changes at two sites in the amino acid sequence. This second PCR product can then be used as a template in a third reaction to form a product DNA sequence encoding a mutant SPE-A toxin with changes at three sites in the amino acid sequence. This method can be utilized to generate DNA sequences encoding mutant toxins having more than one change in the amino acid sequence.

An alternative method to prepare DNA sequences encoding more than one change is to prepare fragments of DNA sequence encoding the change or changes in amino acid sequence by automated synthesis. The fragments can then be subcloned into the wild type SPE-A coding sequence using several unique restriction sites. Restriction sites are known

EXAMPLE 6

Toxicity Studies Related to Single and Double Mutants

Figure 7:
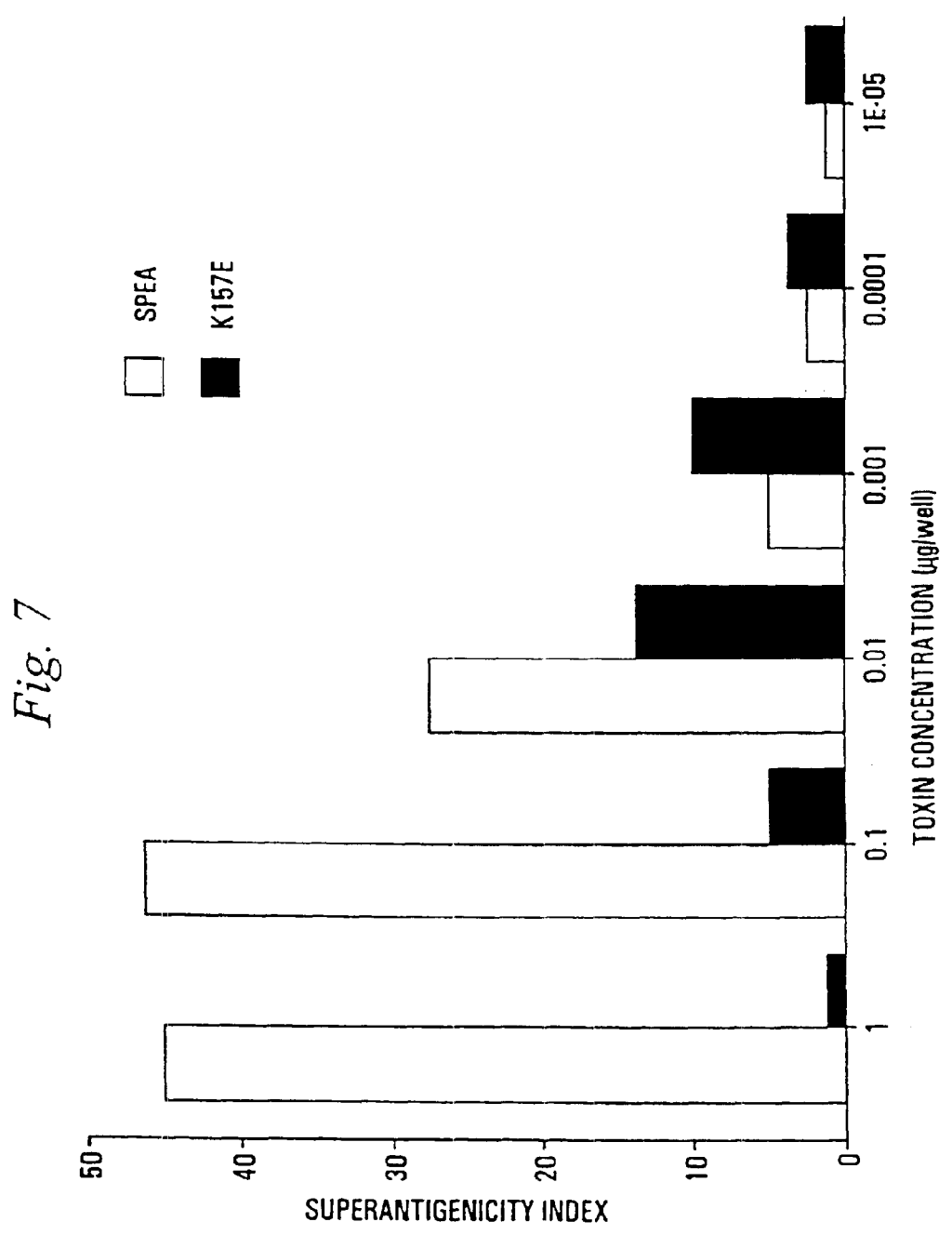
Figure 8:
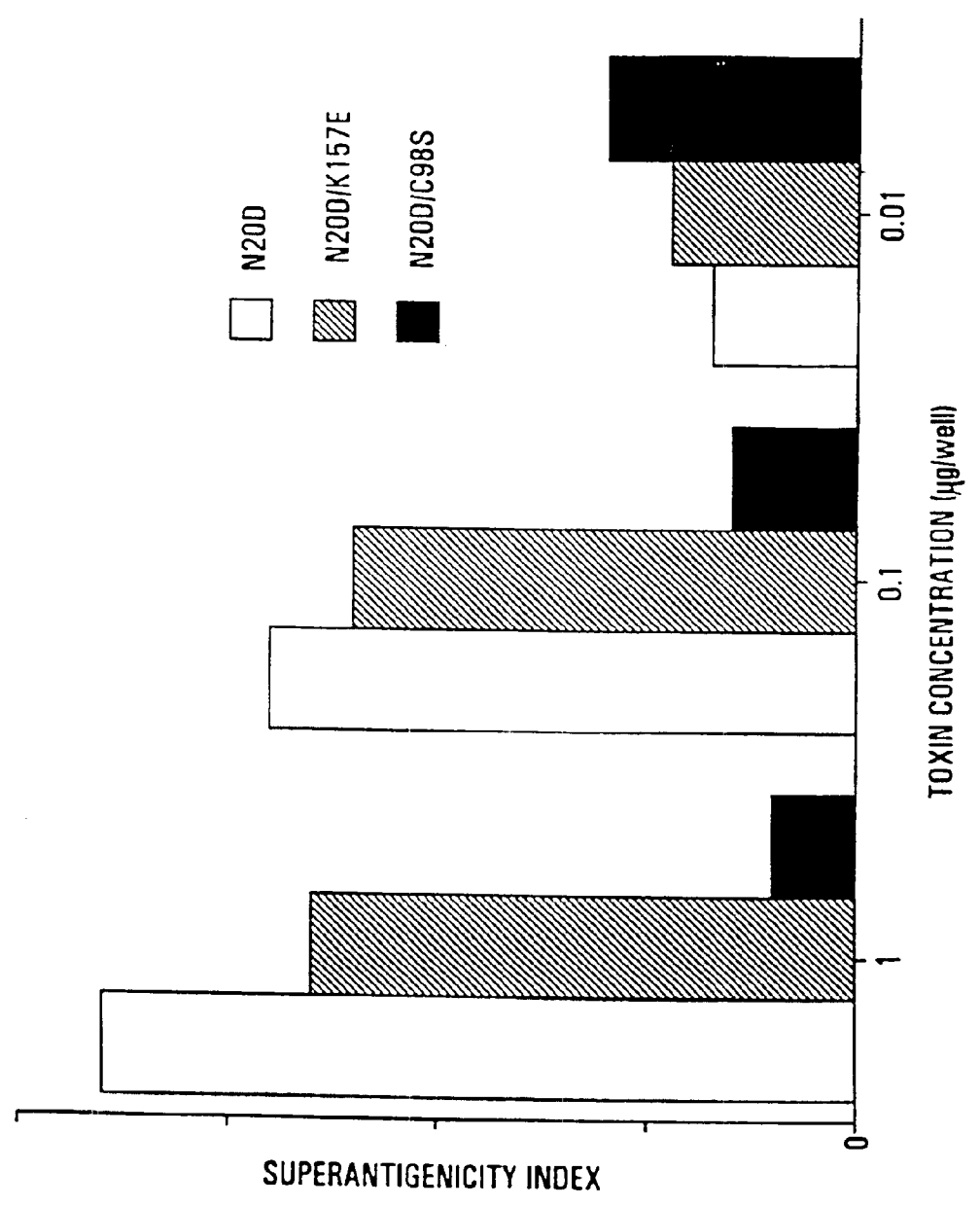

Wild type SPEA, SPEA N20D, SPEA K157E, SPEA N20/C98S, and SPEA N20D/K157E were evaluated for superantigenicity based on their capacity to stimulate rabbit splenocyte proliferation (see FIGS. 7 and 8).

Double mutants SPEA (N20D/C98S, N20D/K157E) were prepared by PCR mutagenesis using the techniques described above. The mutant SPEA gene, speA N20D, served as template DNA for introduction of the second mutation. The double is mutant genes were sequenced as described above to insure that only the indicated changes were present. Only the desired changes were present.

Rabbit spleen cells were cultured in the presence of SPEA and SPEA mutants in vitro for 3 days and then an additional day after addition of 1 $\mu$Ci/well of $^3$H thymidine. Incorporation of $^3$H thymidine into lymphocyte DNA was used as the measure of T cell proliferation. A superantigenicity index was calculated as average counts/min $^3$H thymidine incorporation in stimulated cells divided by average counts/min in cells cultured without added SPEA or mutants.

Wild type SPEA was significantly superantigenic at doses from 1 to 0.001 $\mu$g/well (FIG. 7). SPEA K157E was significantly mitogenic at doses of 0.01 and 0.001 $\mu$g/well (FIG. 7). The three other SPEA mutants (SPEA N20D, SPEA N20D/C98S, SPEA N20D/K157E) were significantly less superantigenic (FIG. 8) than wild type SPEA at doses of 1 to 0.001 $\mu$g (p<0.001). Interestingly, SPEA N20D was significantly more superantigenic (FIG. 8) than SPEA N20D/C98S at doses of 1 and 0.1 $\mu$g (p<0.0005, p<0.001, respectively). Furthermore, SPEA N20D was more mitogenic than SPEA N20D/K157E at the 1 $\mu$g/well dose (p<0.01). Thus, the data indicated the N20D/C98S mutant had less toxicity than the single N20D mutant, and the double mutant N20D/K157E was intermediate between the other two proteins. All three mutants were significantly less toxic than wild type SPEA.

In a second experiment rabbits (3/group) were challenged iv with 10 $\mu$g/kg SPEA or mutants and then endotoxin 5 $\mu$g/kg) 4 hours later. Animals were monitored for 48 hours for enhanced lethality due to administration of SPE and endotoxin. This assay is the most sensitive in vivo measure of SPEA lethal activity. As indicated in Table 6, 0/3 animals challenged with wild type SPEA and endotoxin survived. In contrast all but one animal challenged with SPEA N20D survived, and all animals challenged with SPEA N20D/C98S or SPEA N20D/K157E survived.

TABLE 6

Capacity of SPEA (10 $\mu$g/kg) or mutants (10 $\mu$g/kg) to enhance rabbit susceptibility to the lethal effects of endotoxin (5 $\mu$g/kg)

| SPEA or Mutant | Number Dead/Total |
|---|---|
| Wild type SPEA | 3/3 |
| SPEA N20D | 1/3 |
| SPEA N20D/C98S | 0/3 |

TABLE 6-continued

Capacity of SPEA (10 $\mu$g/kg) or mutants (10 $\mu$g/kg) to enhance rabbit susceptibility to the lethal effects of endotoxin (5 $\mu$g/kg)

| SPEA or Mutant | Number Dead/Total |
|---|---|
| SPEA N20D/K157E | 0/3 |

Note:
SPEA or mutants were administered iv at 0 hour and endotoxin iv at 4 hours.
Animals were monitored for 48 hours for lethality.

In a third experiment rabbits were immunized with SPEA N20D, SPEA N20D/C98S, OR SPEA N20D/K157E, and then challenged with wild type SPEA (10 $\mu$g/kg) and endotoxin (5 $\mu$g/kg or 25 $\mu$g/kg) as in the preceding experiment. Control animals were not immunized but were challenged with wild type SPEA plus endotoxin. Rabbits were immunized every other week for two injections, with mutant proteins (50 $\mu$g/injection) emulsified in incomplete adjuvant (Freund's, Sigma Chemical Co., St Louis, Mo.) and then rested one week prior to challenge with wild type toxin. The combination of wild type SPEA and endotoxin represent 20 $LD_{50}$ for challenge with 10 $\mu$g/kg SPEA and 5 $\mu$g/kg endotoxin, and 100 $LD_{50}$ for challenge with 10 $\mu$g/kg SPEA and 25 $\mu$g/kg endotoxin.

As indicated in Table 7, all animals challenged with 100 $LD_{50}$ of SPEA and endotoxin succumbed. Similarly, all animals immunized with SPEA N20D or N20D/K157E succumbed when challenged with 20 $LD_{50}$ of SPEA and endotoxin. In contrast, animals immunized with the double mutant N20D/C98S survived. Animals immunized with the double mutant N20D/K157E succumbed earlier than other animals. The data above indicates that double mutants and in particular SPEA N20D/C98S shows effectiveness as a toxoid vaccine in test animals.

TABLE 7

Ability of SPEA mutants to immunize rabbits against the capacity of wild type SPEA to enhance susceptibility to lethal endotoxin shock.

| Immunizing Agent | Challenge dose of SPEA and Endotoxin | Number Dead/Total |
|---|---|---|
| None | 10 $\mu$g/kg SPEA, 25 $\mu$g/kg endotoxin | 3/3 |
| SPEA N20D | 10 $\mu$g/kg SPEA, 25 $\mu$g/kg endotoxin | 2/2 |
| SPEA N20D/C98S | 10 $\mu$g/kg SPEA, 25 $\mu$g/kg endotoxin | 2/2 |
| SPEA N20D/K157E | 10 $\mu$g/kg SPEA, 25 $\mu$g/kg endotoxin | 2/2 |
| None | 10 $\mu$g/kg SPEA, 5 $\mu$g/kg endotoxin | 3/3 |
| SPEA N20D | 10 $\mu$g/kg SPEA, 5 $\mu$g/kg endotoxin | 2/2 |
| SPEA N20D/C98S | 10 $\mu$g/kg SPEA. 5 $\mu$g/kg endotoxin | 0/3 |
| SPEA N20D/K157E | 10 $\mu$g/kg SPEA, 5 $\mu$g/kg endotoxin | 3/3 |

Note:
Some animals escaped during this experiment.
These animals were not included in the above data.

EXAMPLE 7

SPE A Inhibition by Antibodies to SPE-A Mutants and SPE-A Mutant Immunization One ml of blood was drawn from the marginal ear vein from each of the rabbits immunized with N20D, N20D/C98S, and N20D/K157E SPEA and nonimmunized controls. Animals were bled 6 days after the last immunization (one day before animals were used in the experiment in Table 6).

Figure 9:
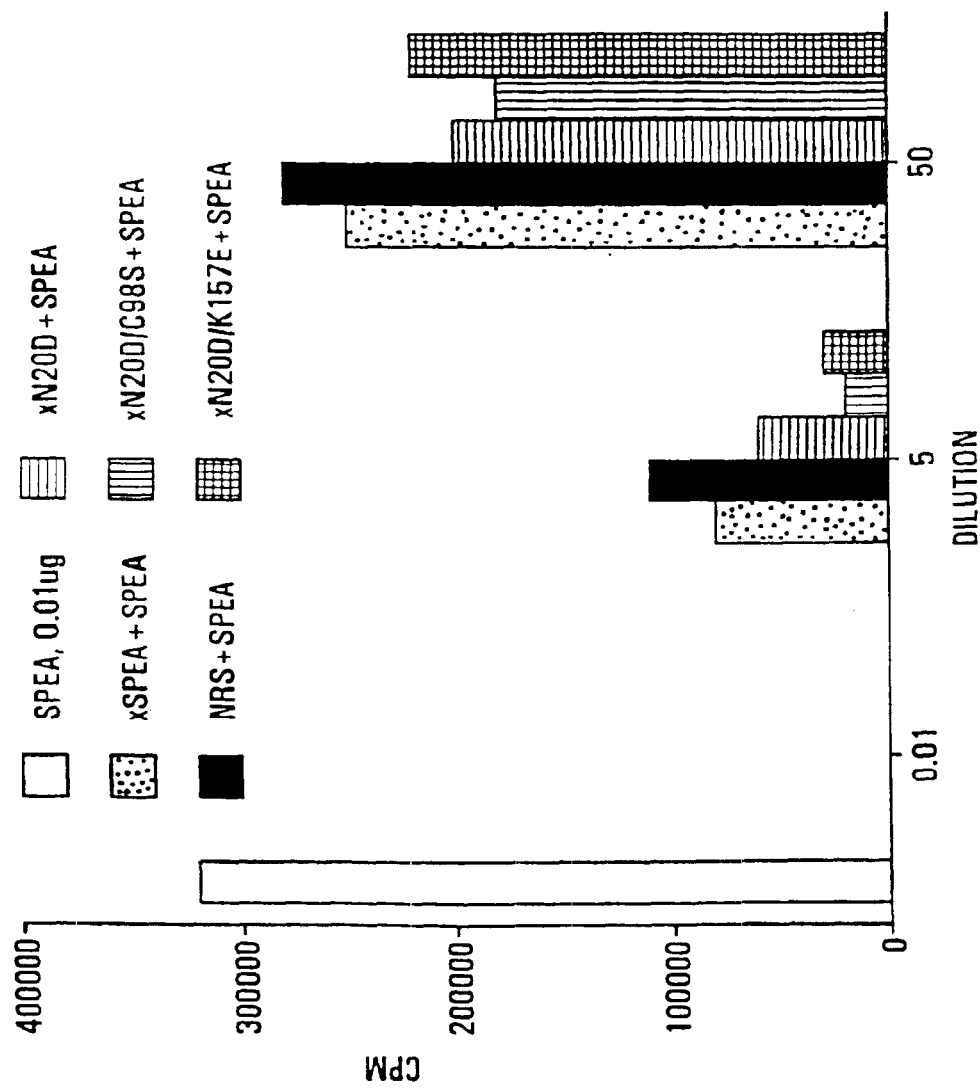
FIG. 9. SPE A Inhibition by Immunized Rabbit Sera. Rabbit sera from rabbits immunized with single and double mutants was used to demonstrate the ability of the sera to neutralize splenocyte mitogenicity in the presence of SPEA.

After the blood clotted, sera were separated by centrifugation (13,000×g, 10 min). Sera from each group were pooled and treated with 33⅓% (final concentration) of to those of skill of the art and can be readily determined from the DNA sequence of a wild type SPE-A toxin. The cloning can be done in a single step with a three fragment ligation method as described by Revi et al. *Nucleic Acid Res.* 16: 1030 (1988).

ammonium sulfate for 1 hr at room temperature to precipitate immunoglobulins. Precipitated immunoglobulins were collected by centrifugation (13,00×g, 10 min), resolubilized to the original volume in phosphate-buffered saline (0.005M NaPO$_4$pH7.0, 0.15M NaCl), and dialyzed for 24 hr against 1 liter of 0.15M NaCl at 4° C. The dialysates were filter sterilized (0.45 μm pore size) and used in studies to neutralize rabbit splenocyte mitogenicity (superantigenicity) of 0.01 μg SPEA (FIG. 9). Serum from one rabbit immunized with sublethal doses of wild type SPEA was fractionated comparably and used as the positive control. Twenty microliters of the immunoglobulin fractions (Igs) from each group of sera were diluted 1/5 and 1/50 with complete RPMI 1640 mammalian cell culture media (dilution with respect to the original serum volume) and added to each of 4 wells containing wild type SPEA and 2×10$^5$ rabbit splenocytes in our standard mitogenicity assay. Igs and wild type toxin were both added to lymphocytes at time 0. The results are shown in FIG. 9.

The 1/5 diluted Igs, whether from immunized animals or nonimmune controls were inhibitory to splenocyte proliferation, probably because of residual ammonium is sulfate in the Igs. However, Igs from the SPEA immune animals and Igs from N20D, N20D/C98S, and N20D/K157E immune animals were more inhibitory than Igs from nonimmune controls (p=0.006 for SPEA versus nonimmune, f=0.035 for N20D versus nonimmune, p=0.0002 for N20D/C98S versus nonimmune, and p=0.0001 for N20D/K157E versus nonimmune by use of Student's t test analysis of normally distributed unpaired data), indicating specific inhibition of mitogenicity.

When Igs were added at the 1/50 dilution, the double mutant N20D/C98S caused significant inhibition of splenocyte proliferation compared to nonimmune controls (p=0.046). At this Ig concentration none of the fractions caused nonspecific suppression of lymphocyte mitogenicity.

These data suggest that the double mutant N20D/C98S was better able to immunize animals against mitogenicity of the wild type SPEA than the single mutant N20D or the other double mutant N20D/K157E. However, the double mutant N20D/K157E was a better immunogen than the single mutant N20D. Without being bound by the following, it is possible the two changes in the N20D/C98S mutant interfere with host cell receptor sites required for lethality, T cell receptor interaction, and possibly indirectly, class II MHC interaction on antigen presenting cells. Since class II MHC interaction depends on amino acid residues in the β barrel domain (domain B) in the standard view of the toxin, we propose also that a change in this region (such as D45N) may improve the immunogenicity of N20D/C98S even more. The basis for this hypothesis is that wild type toxin (and possibly mutants lacking changes in the class II MHC interaction domain) bind directly to class II MHC molecules without the requirement for normal processing by antigen presenting cells. Mutants that contain amino acid changes that interfere with this direct class II MHC interaction may be more immunogenic since the mutants maybe more easily internalized and processed. Thus, the triple mutant N20D/C98S/D45N will be evaluated using the methods used to evaluate the other mutants.

Sera obtained from the nonimmune controls and each group of N20D, N20D/C98S, or N20D/K157E immunized rabbits were tested directly for ELISA titer against wild type SPEA (L. Hudson and F. C. Hay, Practical Immunology 2nd Ed, 1980, Blackwell Scientific Publications, Boston p 237–239.) Serum from each animal was evaluated separately. The antibody titers obtained were averaged and are shown in Table 8. Nonimmune control animals as expected had very low titers of antibodies against SPEA. In contrast all animals immunized against the mutants had significant antibody titers. The animals immunized with the double mutant N20D/K157E had the highest average titer with the titers for the N20D immunized animals was much greater (20, 40, 160, 640, 640 for each of the 6 animals) than either of the double mutants. The data suggest the double mutants gave more consistent immunization.

TABLE 8

ELISA antibody titers of animals immunized against N20D, N20D/C98S, N20D/K157E SPEA and nonimmune controls

| Immunizing Agent | Average Antibody Titer[a] | Range[b] |
|---|---|---|
| None | 10 | <10–20 |
| N20D SPEA | 250 | 20–640 |
| N20D/C98S SPEA | 80 | 80 |
| N20D/K157E SPEA | 425 | 320–640 |

[a]6 animals/group
[b]The lowest titer detectable was 10. Titer is the reciprocal of the last dilution that gave a positive result.

In a final experiment animals (3/group) were immunized against N20D, N20D/C98S, or N20D/K157E (50 μg/injection iv) by administering mutant protein every other day for 5 injections and then resting the animals for one day. Animals were then evaluated for immunity against the ability of wild type SPEA to cause fever [20 times the minimum pyrogenic dose (MPD) 4 hours after injection/kg body weight (20 MPD-4)]. SPEA is one of the most potent pyrogens known with one MPD-4 in rabbits of 0.15 μg/kg. At the 4 hr timepoint animals were injected with endotoxin (25 μg/kg) to evaluate immunity to the enhanced susceptibility, to endotoxin shock. The results are shown in Table 9.

The nonimmune animals and those immunized with N20D SPEA showed both significant fever responses (0.8° C. for both groups) and enhanced susceptibility to endotoxin (⅔ succumbed in 48 hr in both groups). In contrast animals immunized with either double mutant were completely protected from fever and the enhancement phenomenon.

Collectively, all of the above data suggest both double mutants are better able to immunize animals against the toxic effects of SPEA than the single mutant. None of the mutants themselves were toxic to the animals. The double mutant N20D/C98S was a better immunogen than N20D/K157E, but both were effective.

TABLE 9

Ability of SPEA mutants N20D, N20D/C98S, and N20D/K157E to immunize rabbits against SPEA pyrogenicity and lethal challenge by SPEA and endotoxin.

| Immunizing Agent | Fever Response Change ° C. at 4 hr | Number Dead/Total |
|---|---|---|
| None | 0.8 | 2/3 |
| N20D SPEA | 0.8 | 2/3 |
| N20D/C98S SPEA | 0.0 | 0/3 |
| N20D/K157E SPEA | 0.1 | 0/3 |

Although the invention has been described in the context of particular embodiments, it is intended that the scope of coverage of the patent not be limited to those particular embodiments, but is determined by reference to the following claims.

What is claimed is:

1. An isolated nucleic acid molecule comprising a sequence encoding the polypeptide of SEQ ID NO: 14 with aspartic acid, glutamic acid, lysine, or arginine substituted for asparagine-20.

2. The isolated nucleic acid molecule of claim 1 encoding the polypeptide of SEQ ID NO: 14, further comprising serine, alanine, glycine, or threonine substituted for cysteine-98.

3. The isolated nucleic acid molecule of claim 1 encoding the polypeptide of SEQ ID NO: 14, fiber comprising a substitution at aspartic acid-45.

4. The isolated nucleic acid molecule of claim 3 encoding the polypeptide of SEQ ID NO: 14, further comprising serine, alanine, glycine, or threonine substituted for cysteine-98.

5. The isolated nucleic acid molecule of claim 1 encoding the polypeptide of SEQ ID NO: 14, further comprising glutamic acid or aspartic acid substituted for lysine-157.

6. The isolated nucleic acid molecule of claim 1, encoding substitution of aspartic acid for asparagine-20.

7. The isolated nucleic acid molecule of claim 2, encoding substitution of serine for cysteine-98.

8. The isolated nucleic acid molecule of claim 3, encoding substitution of asparagine for aspartic acid-45.

9. The isolated nucleic acid molecule of claim 4, encoding substitution of serine for cyteine-98.

10. The isolated nucleic acid molecule of claim 5, encoding substitution of glutamic acid for lysine-157.

11. An isolated nucleic acid molecule comprising a sequence encoding the polypeptide of SEQ ID NO: 14 with asparagine substituted for lysine-16.

12. An isolated nucleic acid molecule comprising a sequence encoding the polypeptide of SEQ ID NO: 14 with serine, alanine, glycine, or threonine substituted for cysteine-87.

13. The isolated nucleic acid molecule of claim 12, encoding substitution of serine for cysteine-87.

14. An isolated nucleic acid molecule comprising a sequence encoding the polypeptide of SEQ ID NO 14 with serine, alanine, glycine, or threonine substituted for cysteine-90.

15. The isolated nucleic acid molecule of claim 14, encoding substitution of serine for cysteine-90.

16. A recombinant nucleic acid construct comprising:

a polynucleotide comprising the sequence of SEQ ID NO: 12;

a polynucleotide having 99% sequence identity with SEQ ID NO: 12 ard encoding a polypeptide having reduced lethality compared to a wild-type SPEA toxin; or a polynucleotide comprising nucleotides 918–1580 of sequence SEQ ID NO: 12;

operably linked to a promoter.

17. The recombinant nucleic acid construct of claim 16, comprising a polynucleotide having the sequence of SEQ ID NO: 12.

18. The recombinant nucleic acid construct of claim 16, comprising a polynucleotide having 99% sequence identity with SEQ ID NO: 12 and encoding a polypeptide having reduced lethality compared to a wild-type SPE-A toxin.

19. The recombinant nucleic acid construct of claim 16, comprising apolynucleotide having nucleotides 918–1580 of sequence SEQ ID NO; 12.

* * * * *

UNITED STATES PATENT AND TRADEMARK OFFICE
CERTIFICATE OF CORRECTION

PATENT NO. : 6,870,042 B1
DATED : March 22, 2005
INVENTOR(S) : Schlievert et al.

It is certified that error appears in the above-identified patent and that said Letters Patent is hereby corrected as shown below:

Column 1,
Line 10, insert the following paragraph:
-- Government Support
This invention was made with government support under Grant No. HL36611 from the U.S. National Institutes of Health. The government has certain rights in the invention. --.

Column 2,
Line 2, "TNT-α" should read -- TNF-α --.
Line 17, after "this pathology." insert the following sentence -- Certain single amino acid substitutions in central regions of the SPE-A molecule have been shown to affect the mitogenic activity of and binding to a HLA class II molecules by SPE-A (Hartwig et. al. International Immunology 5:5, 869-875 (1993)). --.
Line 32, "to human umbilical" should read -- to the human umbilical --.

Column 9,
Line 47, "useful in vaccine is" should read -- useful in vaccine --.

Column 12,
Line 33, "wild is type SPEA." should read -- wild type SPEA. --.

Column 13,
Line 47, "viva using fluorescence" should read -- vivo using fluorescence --.

Column 14,
Line 7, "amino aced sequence" should read -- amino acid sequence --.
Line 50, "wild type is SPE-A toxin" should read -- wild type SPE-A toxin --.
Line 67, "Compostions or" should read -- Compositions or --.

Column 16,
Line 67, "and 31 flanking" should read -- and 3' flanking --.

Column 18,
Line 39, "in Example S." should read -- in Example 5. --.
Line 51, "with chances in amino acid" should read -- with changes in amino acid --.

Column 22,
Line 49, "pBR328 (carrying Amp and" should read -- pBR328 (carrying Amp and Tet --.

UNITED STATES PATENT AND TRADEMARK OFFICE
CERTIFICATE OF CORRECTION

PATENT NO. : 6,870,042 B1
DATED : March 22, 2005
INVENTOR(S) : Schlievert et al.

It is certified that error appears in the above-identified patent and that said Letters Patent is hereby corrected as shown below:

Columns 25-26,
Line 48,
"5' -CCC CCC <u>GTC GAC</u> GAT AAA ATA GTT GCT AAG CTA CAA GCT-3' (SEQ ID NO:2)
                  Sal I"
should be in column 26 and not in column 25.

Column 31,
Line 20, "The double is mutant genes" should read -- The double mutant genes --.

Column 34,
Lines 5-6, "average titer with the titers" should read -- average titer with the other two mutants being comparable. However, the range of titers --.

Column 45,
Line 11, "fiber comprising a" should read -- further comprising a --.

Column 46,
Line 16, "ard encoding a polypeptide" should read -- and encoding a polypeptide --.
Line 17, "wild-type SPEA toxin; or" should read -- wild-type SPE-A toxin; or --.
Line 31, "comprising apolynucleotide" should read -- comprising a polynucleotide --.

Signed and Sealed this

Sixth Day of September, 2005

JON W. DUDAS
*Director of the United States Patent and Trademark Office*

SEQUENCE LISTING

<160> NUMBER OF SEQ ID NOS: 14

<210> SEQ ID NO 1
<211> LENGTH: 29
<212> TYPE: DNA
<213> ORGANISM: Artificial Sequence
<220> FEATURE:
<223> OTHER INFORMATION: Primers for producing mutants

<400> SEQUENCE: 1
ccatcacggg tggattcttg aaacaggtg                                29

<210> SEQ ID NO 2
<211> LENGTH: 47
<212> TYPE: DNA
<213> ORGANISM: Artificial Sequence
<220> FEATURE:
<223> OTHER INFORMATION: Primers for producing mutants

<400> SEQUENCE: 2
ccatcacgcc ccccgtcgac gataaaatag ttgctaagct acaagct          47

<210> SEQ ID NO 3
<211> LENGTH: 172
<212> TYPE: DNA
<213> ORGANISM: Artificial Sequence
<220> FEATURE:
<223> OTHER INFORMATION: Primers for producing mutants

<400> SEQUENCE: 3
ccatcaccat caccaagaag aaataattac atattaaata caatacatat gtaataataa    60
taaatatata aataaaataa ttacatatta aaaataatac ttaattataa aaacactata   120
atttccataa atattaataa ataattaaaa ataaaataat aaataattaa tc          172

<210> SEQ ID NO 4
<211> LENGTH: 172
<212> TYPE: DNA
<213> ORGANISM: Artificial Sequence
<220> FEATURE:
<223> OTHER INFORMATION: Primers for producing mutants

<400> SEQUENCE: 4
ccatcaccat caccaagaag aaataattac atattaaata caatacatat gtaataataa    60
taaatatata aataaaataa ttacatatta aaaataatac ttaattataa aaacactata   120
atttccataa atattaataa ataattaaaa ataaaataat aaataattaa tc          172

<210> SEQ ID NO 5
<211> LENGTH: 172
<212> TYPE: DNA
<213> ORGANISM: Artificial Sequence
<220> FEATURE:
<223> OTHER INFORMATION: Primers for producing mutants

<400> SEQUENCE: 5
ccatcaccat caccaagaag aaataattac atattaaata caatacatat gtaataataa    60
taaatatata aataaaataa ttacatatta aaaataatac ttaattataa aaacactata   120
atttccataa atattaataa ataattaaaa ataaaataat aaataattaa tc          172

<210> SEQ ID NO 6
<211> LENGTH: 172

```
<212> TYPE: DNA
<213> ORGANISM: Artificial Sequence
<220> FEATURE:
<223> OTHER INFORMATION: Primers for producing mutants

<400> SEQUENCE: 6
ccatcaccat caccaagaag aaataattac atattaaata caatacatat gtaataataa      60
taaatatata aataaaataa ttacatatta aaaataatac ttaattataa aaacactata     120
atttccataa atattaataa ataattaaaa ataaaataat aaataattaa tc             172

<210> SEQ ID NO 7
<211> LENGTH: 172
<212> TYPE: DNA
<213> ORGANISM: Artificial Sequence
<220> FEATURE:
<223> OTHER INFORMATION: Primers for producing mutants

<400> SEQUENCE: 7
ccatcaccat caccaagaag aaataattac atattaaata caatacatat gtaataataa      60
taaatatata aataaaataa ttacatatta aaaataatac ttaattataa aaacactata     120
atttccataa atattaataa ataattaaaa ataaaataat aaataattaa tc             172

<210> SEQ ID NO 8
<211> LENGTH: 172
<212> TYPE: DNA
<213> ORGANISM: Artificial Sequence
<220> FEATURE:
<223> OTHER INFORMATION: Primers for producing mutants

<400> SEQUENCE: 8
ccatcaccat caccaagaag aaataattac atattaaata caatacatat gtaataataa      60
taaatatata aataaaataa ttacatatta aaaataatac ttaattataa aaacactata     120
atttccataa atattaataa ataattaaaa ataaaataat aaataattaa tc             172

<210> SEQ ID NO 9
<211> LENGTH: 60
<212> TYPE: DNA
<213> ORGANISM: Artificial Sequence
<220> FEATURE:
<223> OTHER INFORMATION: Primers for producing mutants

<400> SEQUENCE: 9
ccatcaccat caccaagaag aaataattac atattaaata caatacatat gtaataataa      60

<210> SEQ ID NO 10
<211> LENGTH: 112
<212> TYPE: DNA
<213> ORGANISM: Artificial Sequence
<220> FEATURE:
<223> OTHER INFORMATION: Primers for producing mutants

<400> SEQUENCE: 10
taaatatata aataaaataa ttacatatta aaaataatac ttaattataa aaacactata      60
atttccataa atattaataa ataattaaaa ataaaataat aaataattaa tc             112

<210> SEQ ID NO 11
<211> LENGTH: 172
<212> TYPE: DNA
<213> ORGANISM: Artificial Sequence
<220> FEATURE:
<223> OTHER INFORMATION: Primers for producing mutants
```

<400> SEQUENCE: 11

| | | |
|---|---|---|
| ccatcaccat caccaagaag aaataattac atattaaata caatacatat gtaataataa | 60 |
| taaatatata aataaaataa ttacatatta aaaataatac ttaattataa aaacactata | 120 |
| atttccataa atattaataa ataattaaaa ataaaataat aataattaa tc | 172 |

<210> SEQ ID NO 12  
<211> LENGTH: 1851  
<212> TYPE: DNA  
<213> ORGANISM: Streptococcus pyogenes  
<220> FEATURE:  
<221> NAME/KEY: CDS  
<222> LOCATION: (828)..(1583)  
<223> OTHER INFORMATION:

<400> SEQUENCE: 12

| | |
|---|---|
| ccatcacgca tcactcatgt ttgacagctt atcatcgata agcttacttt tcgaatcagg | 60 |
| tctatccttg aaacaggtgc aacatagatt agggcatgga gatttaccag acaactatga | 120 |
| acgtatatac tcacatcacg caatcggcaa ttgatgacat tggaactaaa ttcaatcaat | 180 |
| tgttactaa caagcaacta gattgacaac taattctcaa caaacgttaa tttaacaaca | 240 |
| tcaagtaac tcccaccagc tccatcaatg cttaccgtaa gtaatcataa cttactaaaa | 300 |
| ccttgttaca tcaaggtttt ttcttttttgt cttgttcatg agttaccata actttctata | 360 |
| ttattgacaa ctaaattgac aactcttcaa ttattttttct gtctactcaa agttttcttc | 420 |
| atttgatata gtctaattcc accatcactt cttccactct ctctaccgtc acaacttcat | 480 |
| catctctcac ttttttcgtgt ggtaacacat aatcaaatat ctttccgttt ttacgcacta | 540 |
| tcgctactgt gtcacctaaa atataccccct tatcaatcgc ttctttaaac tcatctatat | 600 |
| ataacatatt tcatcctcct acctatctat tcgtaaaaag ataaaaataa ctattgtttt | 660 |
| ttttgttatt ttataataaa attattaata taagttaatg tttttttaaaa atatacaatt | 720 |
| ttattctatt tatagttagc tatttttttca ttgttagtaa tattggtgaa ttgtaataac | 780 |

| | | |
|---|---|---|
| cttttttaaat ctagaggaga acccagatat aaaatggagg aatatta atg gaa aac | 836 |
| | Met Glu Asn | |
| | 1 | |

| | | |
|---|---|---|
| aat aaa aaa gta ttg aag aaa atg gta ttt ttt gtt tta gtg aca ttt | 884 |
| Asn Lys Lys Val Leu Lys Lys Met Val Phe Phe Val Leu Val Thr Phe | |
| 5 | 10 | 15 |

| | | |
|---|---|---|
| ctt gga cta aca atc tcg caa gag gta ttt gct caa caa gac ccc gat | 932 |
| Leu Gly Leu Thr Ile Ser Gln Glu Val Phe Ala Gln Gln Asp Pro Asp | |
| 20 | 25 | 30 | 35 |

| | | |
|---|---|---|
| cca agc caa ctt cac aga tct agt tta gtt aaa aac ctt caa aat ata | 980 |
| Pro Ser Gln Leu His Arg Ser Ser Leu Val Lys Asn Leu Gln Asn Ile | |
| | 40 | 45 | 50 |

| | | |
|---|---|---|
| tat ttt ctt tat gag ggt gac cct gtt act cac gag aat gtg aaa tct | 1028 |
| Tyr Phe Leu Tyr Glu Gly Asp Pro Val Thr His Glu Asn Val Lys Ser | |
| 55 | 60 | 65 |

| | | |
|---|---|---|
| gtt gat caa ctt tta tct cac cat tta ata tat aat gtt tca ggg cca | 1076 |
| Val Asp Gln Leu Leu Ser His His Leu Ile Tyr Asn Val Ser Gly Pro | |
| 70 | 75 | 80 |

| | | |
|---|---|---|
| aat tat gat aaa tta aaa act gaa ctt aag aac caa gag atg gca act | 1124 |
| Asn Tyr Asp Lys Leu Lys Thr Glu Leu Lys Asn Gln Glu Met Ala Thr | |
| 85 | 90 | 95 |

| | | |
|---|---|---|
| tta ttt aag gat aaa aac gtt gat att tat ggt gta gaa tat tac cat | 1172 |
| Leu Phe Lys Asp Lys Asn Val Asp Ile Tyr Gly Val Glu Tyr Tyr His | |
| 100 | 105 | 110 | 115 |

| | | |
|---|---|---|
| ctc tgt tat tta tgt gaa aat gca gaa agg agt gca tgt atc tac gga | 1220 |

```
Leu Cys Tyr Leu Cys Glu Asn Ala Glu Arg Ser Ala Cys Ile Tyr Gly
                120                 125                 130 ggg gta aca aat cat gaa ggg aat cat tta gaa att cct aaa aag ata      1268
Gly Val Thr Asn His Glu Gly Asn His Leu Glu Ile Pro Lys Lys Ile
                135                 140                 145 gtc gtt aaa gta tca atc gat ggt atc caa agc cta tca ttt gat att      1316
Val Val Lys Val Ser Ile Asp Gly Ile Gln Ser Leu Ser Phe Asp Ile
                150                 155                 160 gaa aca aat aaa aaa atg gta act gct caa gaa tta gac tat aaa gtt      1364
Glu Thr Asn Lys Lys Met Val Thr Ala Gln Glu Leu Asp Tyr Lys Val
                165                 170                 175 aga aaa tat ctt aca gat aat aag caa cta tat act aat gga cct tct      1412
Arg Lys Tyr Leu Thr Asp Asn Lys Gln Leu Tyr Thr Asn Gly Pro Ser
180                 185                 190                 195 aaa tat gaa act gga tat ata aag ttc ata cct aag aat aaa gaa agt      1460
Lys Tyr Glu Thr Gly Tyr Ile Lys Phe Ile Pro Lys Asn Lys Glu Ser
                200                 205                 210 ttt tgg ttt gat ttt ttc cct gaa cca gaa ttt act caa tct aaa tat      1508
Phe Trp Phe Asp Phe Phe Pro Glu Pro Glu Phe Thr Gln Ser Lys Tyr
                215                 220                 225 ctt atg ata tat aaa gat aat gaa acg ctt gac tca aac aca agc caa      1556
Leu Met Ile Tyr Lys Asp Asn Glu Thr Leu Asp Ser Asn Thr Ser Gln
                230                 235                 240 att gaa gtc tac cta aca acc aag taa cttttgctt ttggcaacct             1603
Ile Glu Val Tyr Leu Thr Thr Lys
                245                 250 tacctactgc tggatttaga aatttttattg caattctttt attaatgtaa aaaccgctca   1663
tttgatgagc ggttttgtct tatctaaagg agctttaccct cctaatgctg caaaatttta   1723
aatgttggat ttttgtattt gtctattgta tttgatgggt aatcccattt ttcgacagac    1783
atcgtcgtgc cacctctaac accaaaatca tagacaggag cttgtagctt agcaactatt    1843
ttatcgtc                                                             1851

<210> SEQ ID NO 13
<211> LENGTH: 251
<212> TYPE: PRT
<213> ORGANISM: Streptococcus pyogenes

<400> SEQUENCE: 13

Met Glu Asn Asn Lys Lys Val Leu Lys Lys Met Val Phe Phe Val Leu
1               5                   10                  15

Val Thr Phe Leu Gly Leu Thr Ile Ser Gln Glu Val Phe Ala Gln Gln
                20                  25                  30

Asp Pro Asp Pro Ser Gln Leu His Arg Ser Ser Leu Val Lys Asn Leu
            35                  40                  45

Gln Asn Ile Tyr Phe Leu Tyr Glu Gly Asp Pro Val Thr His Glu Asn
        50                  55                  60

Val Lys Ser Val Asp Gln Leu Leu Ser His His Leu Ile Tyr Asn Val
65                  70                  75                  80

Ser Gly Pro Asn Tyr Asp Lys Leu Lys Thr Glu Leu Lys Asn Gln Glu
                85                  90                  95

Met Ala Thr Leu Phe Lys Asp Lys Asn Val Asp Ile Tyr Gly Val Glu
            100                 105                 110

Tyr Tyr His Leu Cys Tyr Leu Cys Glu Asn Ala Glu Arg Ser Ala Cys
        115                 120                 125

Ile Tyr Gly Gly Val Thr Asn His Glu Gly Asn His Leu Glu Ile Pro
    130                 135                 140
```

-continued

```
Lys Lys Ile Val Val Lys Val Ser Ile Asp Gly Ile Gln Ser Leu Ser
145                 150                 155                 160

Phe Asp Ile Glu Thr Asn Lys Lys Met Val Thr Ala Gln Glu Leu Asp
                165                 170                 175

Tyr Lys Val Arg Lys Tyr Leu Thr Asp Asn Lys Gln Leu Tyr Thr Asn
            180                 185                 190

Gly Pro Ser Lys Tyr Glu Thr Gly Tyr Ile Lys Phe Ile Pro Lys Asn
        195                 200                 205

Lys Glu Ser Phe Trp Phe Asp Phe Pro Glu Pro Glu Phe Thr Gln
    210                 215                 220

Ser Lys Tyr Leu Met Ile Tyr Lys Asp Asn Glu Thr Leu Asp Ser Asn
225                 230                 235                 240

Thr Ser Gln Ile Glu Val Tyr Leu Thr Thr Lys
                245                 250
```

<210> SEQ ID NO 14
<211> LENGTH: 221
<212> TYPE: PRT
<213> ORGANISM: Streptococcus pyogenes

<400> SEQUENCE: 14

```
Gln Gln Asp Pro Asp Pro Ser Gln Leu His Arg Ser Ser Leu Val Lys
1               5                   10                  15

Asn Leu Gln Asn Ile Tyr Phe Leu Tyr Glu Gly Asp Pro Val Thr His
            20                  25                  30

Glu Asn Val Lys Ser Val Asp Gln Leu Leu Ser His His Leu Ile Tyr
        35                  40                  45

Asn Val Ser Gly Pro Asn Tyr Asp Lys Leu Lys Thr Glu Leu Lys Asn
    50                  55                  60

Gln Glu Met Ala Thr Leu Phe Lys Asp Lys Asn Val Asp Ile Tyr Gly
65                  70                  75                  80

Val Glu Tyr Tyr His Leu Cys Tyr Leu Cys Glu Asn Ala Glu Arg Ser
                85                  90                  95

Ala Cys Ile Tyr Gly Gly Val Thr Asn His Glu Gly Asn His Leu Glu
            100                 105                 110

Ile Pro Lys Lys Ile Val Val Lys Val Ser Ile Asp Gly Ile Gln Ser
        115                 120                 125

Leu Ser Phe Asp Ile Glu Thr Asn Lys Lys Met Val Thr Ala Gln Glu
    130                 135                 140

Leu Asp Tyr Lys Val Arg Lys Tyr Leu Thr Asp Asn Lys Gln Leu Tyr
145                 150                 155                 160

Thr Asn Gly Pro Ser Lys Tyr Glu Thr Gly Tyr Ile Lys Phe Ile Pro
                165                 170                 175

Lys Asn Lys Glu Ser Phe Trp Phe Asp Phe Pro Glu Pro Glu Phe
            180                 185                 190

Thr Gln Ser Lys Tyr Leu Met Ile Tyr Lys Asp Asn Glu Thr Leu Asp
        195                 200                 205

Ser Asn Thr Ser Gln Ile Glu Val Tyr Leu Thr Thr Lys
    210                 215                 220
```